(12) United States Patent
Slishman

(10) Patent No.: US 6,913,587 B2
(45) Date of Patent: *Jul. 5, 2005

(54) ADJUSTABLE SUPPORT

(75) Inventor: Samuel Slishman, Morgan Hill, CA (US)

(73) Assignee: Science & Technology Corporation @ UNM, Albuquerque, NM (US)

( * ) Notice: Subject to any disclaimer, the term of this patent is extended or adjusted under 35 U.S.C. 154(b) by 291 days.

This patent is subject to a terminal disclaimer.

(21) Appl. No.: 10/148,743

(22) PCT Filed: Nov. 29, 2000

(86) PCT No.: PCT/US00/32466
§ 371 (c)(1),
(2), (4) Date: Sep. 6, 2002

(87) PCT Pub. No.: WO01/39715
PCT Pub. Date: Jun. 7, 2001

(65) Prior Publication Data
US 2003/0050588 A1 Mar. 13, 2003

Related U.S. Application Data

(63) Continuation-in-part of application No. 09/450,434, filed on Nov. 30, 1999, now Pat. No. 6,394,972.

(51) Int. Cl.⁷ .................................................. A61F 5/00
(52) U.S. Cl. .............................. 602/32; 602/5; 602/23; 128/869; 128/882; 135/65; 135/68
(58) Field of Search ................................ 602/32, 5, 12, 602/23, 36, 38, 61, 62; 128/99.1, 845, 869, 882; 135/65, 68, 71, 72, 73, 75, 77

(56) References Cited

U.S. PATENT DOCUMENTS

| | | |
|---|---|---|
| 350,526 A | 10/1886 | Bunce |
| 2,058,563 A | 10/1936 | Campbell |
| 2,186,456 A | 1/1940 | Gordon |
| 2,252,258 A | 8/1941 | Hayden |
| 2,260,216 A | 10/1941 | Doyle |
| 2,394,653 A | 2/1946 | Auerhaan |
| 2,398,247 A | 4/1946 | Redcliffe |
| 3,299,888 A | 1/1967 | Muckinhaupt |
| 3,413,971 A | 12/1968 | Evans |
| 3,454,002 A | 7/1969 | Westlake et al. |
| 3,503,390 A | 3/1970 | Peters |
| 3,750,659 A | 8/1973 | Loomans |
| 3,756,227 A | 9/1973 | Sager |
| 3,888,243 A | 6/1975 | Powlan |
| 3,942,521 A | 3/1976 | Klippel |
| 4,485,808 A | * 12/1984 | Hepburn ........................ 602/5 |
| 4,608,971 A | 9/1986 | Borschneck |
| 4,649,907 A | 3/1987 | Whitehead et al. |
| 4,729,453 A | 3/1988 | Lyons, Sr. |
| 4,750,479 A | * 6/1988 | Schawl ........................ 602/32 |
| 4,809,725 A | 3/1989 | Champigny |
| 4,911,152 A | 3/1990 | Barnes et al. |
| 5,019,077 A | 5/1991 | De Bastiani et al. |
| 5,071,119 A | 12/1991 | Johnson |
| 5,181,904 A | 1/1993 | Cook et al. |
| 5,230,700 A | 7/1993 | Humbert et al. |
| 5,342,288 A | 8/1994 | Lee et al. |
| 5,441,307 A | 8/1995 | Quintana et al. |
| 5,636,650 A | 6/1997 | Kroeze |
| 5,681,272 A | * 10/1997 | Lee ............................ 602/32 |

(Continued)

Primary Examiner—Fadi H. Dahbour
(74) Attorney, Agent, or Firm—Roberts Abokhair & Mardula, LLC

(57) ABSTRACT

The present invention provides an adjustable support that may be telescopically extendable, coarsely and finely adjustable, and providing a mechanical advantage while being readily transportable. The adjustable support may have two to three telescoping members that nest inside one another when not is use, and may be triangular, rectangular, or circular in cross section. The adjustable support may be used as a traction splint, a walking stick, ski pole, or a crutch.

66 Claims, 16 Drawing Sheets

U.S. PATENT DOCUMENTS

| | | | |
|---|---|---|---|
| 5,755,245 A | 5/1998 | Van Helvoort | |
| 5,769,104 A | 6/1998 | Uemura | |
| 5,775,334 A | 7/1998 | Lamb et al. | |
| 5,778,914 A | 7/1998 | Trani | |
| 5,807,294 A * | 9/1998 | Cawley et al. | 602/32 |
| 5,944,677 A * | 8/1999 | Richard | 602/23 |
| 5,957,477 A | 9/1999 | Enz et al. | |
| 5,996,602 A | 12/1999 | Cato, III | |
| 6,082,767 A | 7/2000 | Bujold et al. | |
| 6,085,766 A | 7/2000 | Geary | |
| 6,394,972 B1 | 5/2002 | Slishman | |
| 6,443,918 B1 * | 9/2002 | Wang | 602/5 |
| 6,669,659 B2 * | 12/2003 | Dittmer et al. | 602/5 |

* cited by examiner

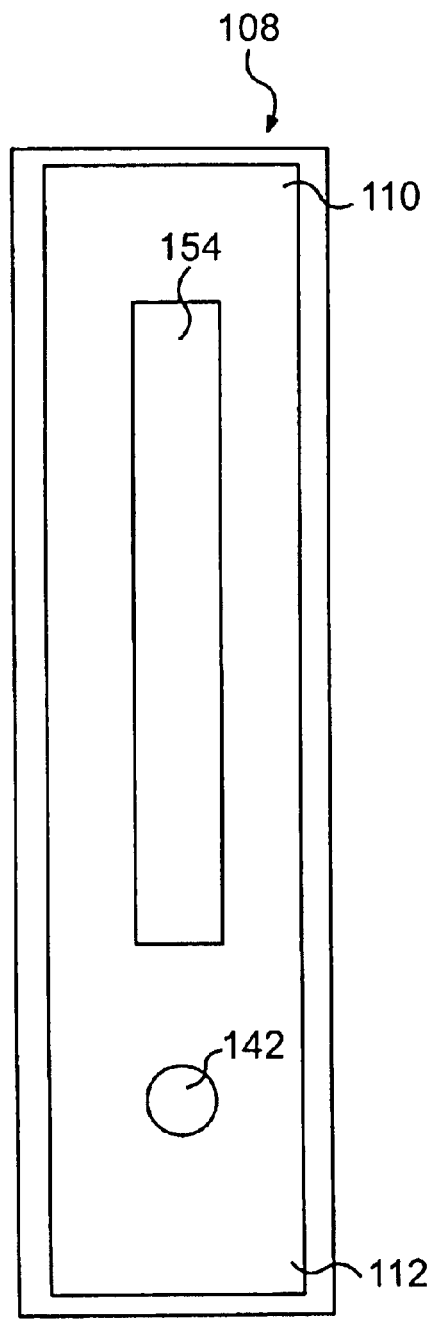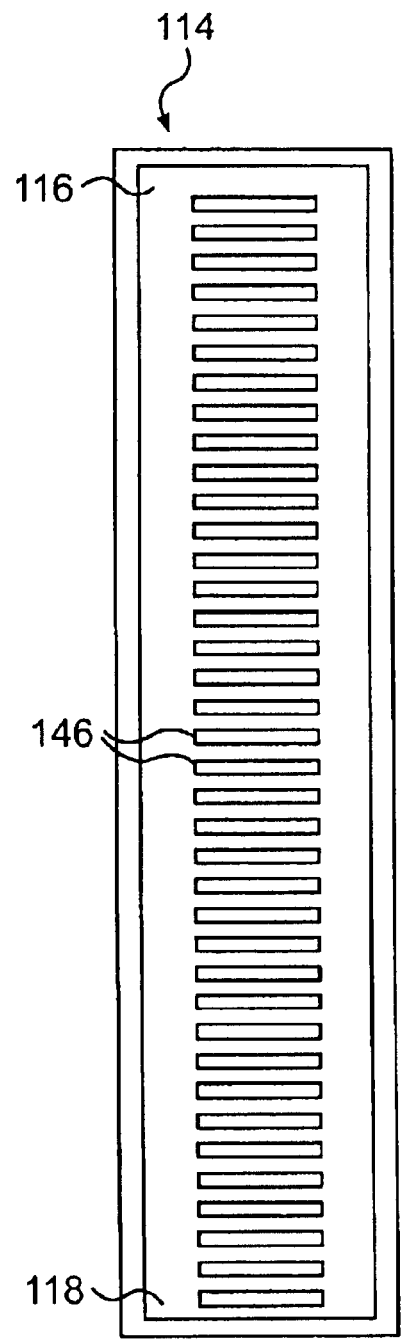
FIG. 1D  FIG. 1E

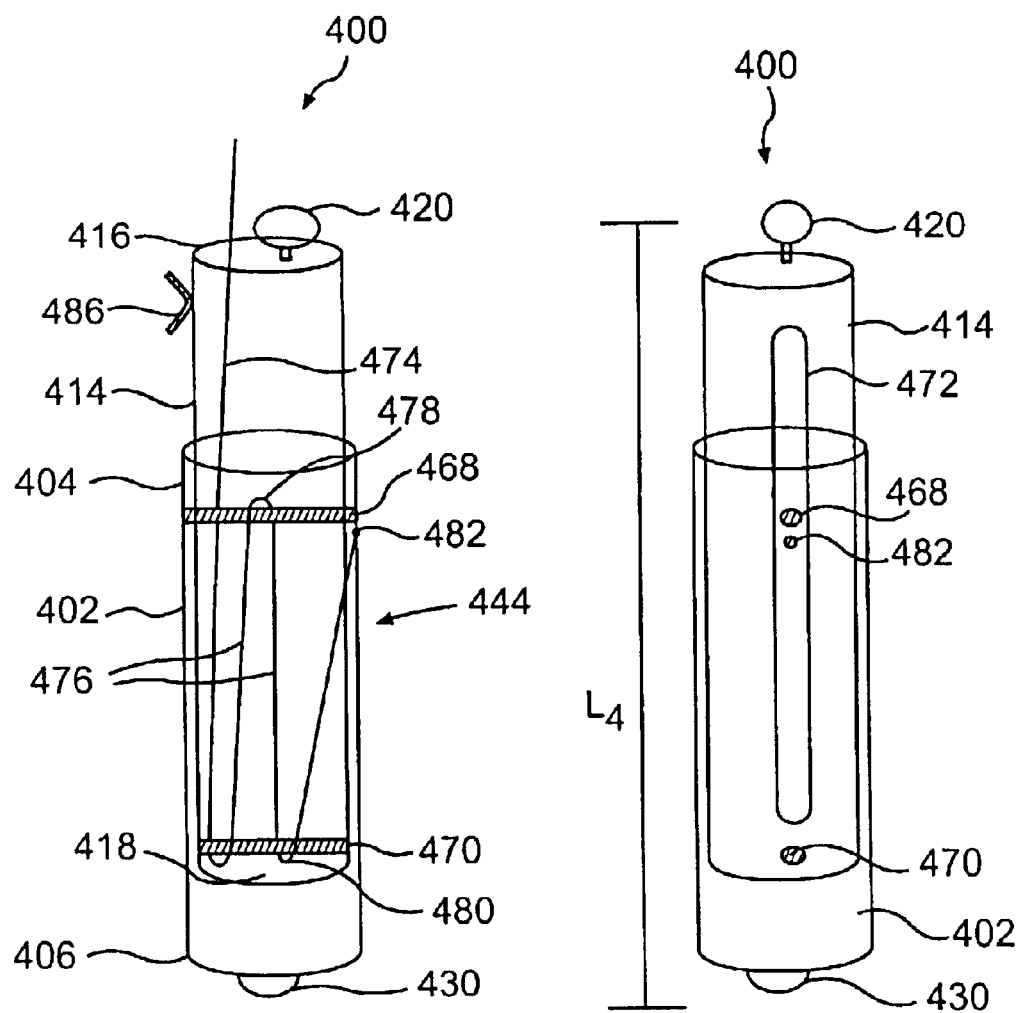
*FIG. 4A*      *FIG. 4B*

ADJUSTABLE SUPPORT

CROSS-REFERENCE TO RELATED APPLICATION

This application is a continuation-in-part and makes reference to U.S. application Ser. No. 09/450,434, entitled "Traction Splint," filed Nov. 30, 1999 now U.S. Pat. No. 6,394,972, the entire contents and disclosure of which is hereby incorporated by reference.

BACKGROUND OF THE INVENTION

1. Field of the Invention

The present invention relates generally to adjustable supports.

2. Description of the Prior Art

There have been several attempts to design portable devices that provide external traction to an injured limb. For example, U.S. Pat. No. 4,608,971 to Borschneck describes an emergency leg splint that telescopes for length adjustment. However, splints like Borschneck's are relatively large and bulky making them difficult to transport and impractical.

Splints designed to be portable such as Borschneck's do not provide significant mechanical advantage, so these splints are less useful for fracture or dislocation reductions. Current traction splints are also generally designed specifically for femoral traction only. Furthermore, current traction splints cannot be adjusted to exactly fit the limb being supported without extension beyond the leg. Nor do current portable splints have functionality in addition to use as a splint.

SUMMARY OF THE INVENTION

It is therefore an object of the present invention to provide a compact, lightweight versatile adjustable support.

It is another object of the present invention to provide an adjustable support having both a coarse and a fine adjustment device.

It is yet another object to provide an adjustable support having a mechanical advantage.

It is yet another object of the present invention to provide a traction splint that may have its length adjusted for use by a particular user.

It is yet another object of the present invention to provide a walking stick that may have its length adjusted for use by a particular user.

It is yet another object of the present invention to provide a crutch that may have its length adjusted for use by a particular user.

It is yet another object of the present invention to provide a traction splint that collapses into an easily portable form.

It is yet another object of the present invention to provide a walking stick that collapses into an easily portable form.

It is yet another object of the present invention to provide a crutch that collapses into an easily portable form.

In a first broad aspect, the present invention provides an adjustable support, comprising: an outer member having a distal end and a proximal end; a middle member slidable in a longitudinal direction within the outer member, the middle member having a distal end and a proximal end; an inner member slidable in a longitudinal direction within the middle member, the inner member having a distal end and a proximal end; a coarse adjustment device for adjusting a distance between the distal end of the middle member and a proximal end of the outer member by a plurality of course increments; and a fine adjustment device for adjusting a distance between the distal end of the inner member and a proximal end of the middle member by a plurality of fine increments.

In a second broad aspect, the present invention provides an adjustable support, comprising: an outer member having a distal end and a proximal end; an inner member slidable in a longitudinal direction within the outer member, the inner member having a distal end and a proximal end; and an adjustment device for adjusting a distance between the distal end of the inner member and a proximal end of the outer member by a plurality of fine increments.

In a third broad aspect, the present invention provides an adjustable support comprising: an elongated member having a distal end and a proximal end; a cord extending through a hollow portion of the elongated member, the cord including; a distal securing device for securing the elongated member to a limb of an individual, the distal securing device being mounted at the distal end of the elongated member and including a loop portion extending from the distal end of the elongated member; a free end for grasping by a user and for allowing a user to pull on the cord to cause the loop portion of the distal securing device to pull the limb of the individual towards the elongated member; a connecting portion connecting the loop portion of the distal securing device to the free end; and proximal securing device for securing the elongated member to the limb of the individual, the proximal securing device being mounted on the elongated member at a position proximal to the distal end of the elongated member.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 1D is a schematic side view of a middle member of the embodiment of FIG. 1A;

FIG. 1E is a schematic side view of an inner member of the embodiment of FIG. 1A;

FIG. 4A is a schematic front view of another embodiment of an adjustable support of the present invention useful as a traction splint;

FIG. 4B is a schematic side view of the embodiment of FIG. 4A;

DETAILED DESCRIPTION OF THE PREFERRED EMBODIMENT

Definitions

Figure 1A:
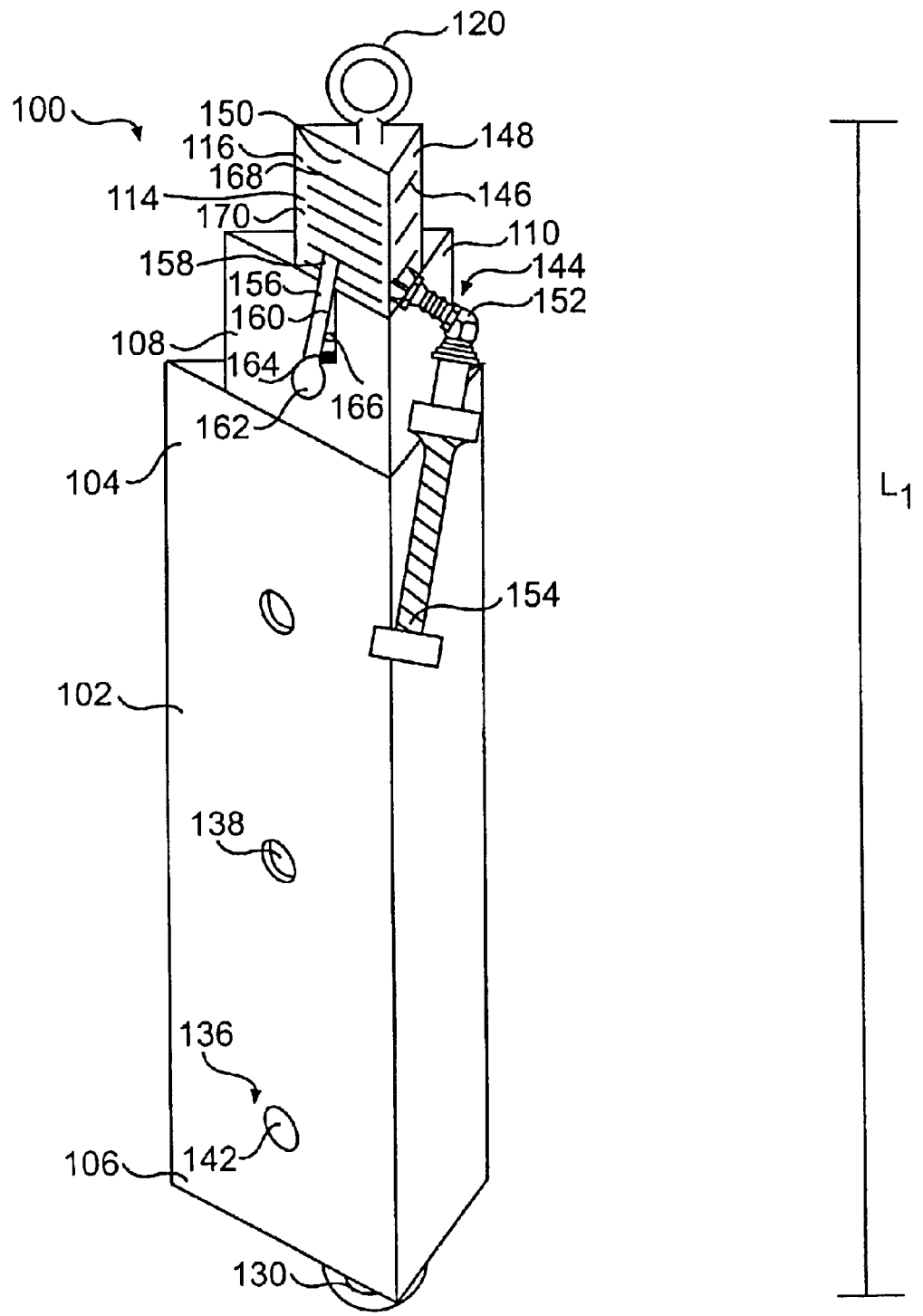
FIG. 1A is a schematic perspective view of an adjustable support of the present invention useful as a traction splint.

For the purposes of the present invention the term "individual" refers to either an individual person or animal on or by whom the adjustable support of the present invention is used.

For the purposes of the present invention, the term "adjustable support" refers to the various devices encompassed by the present invention including traction splints, walking sticks, crutches, etc.

For the purposes of the present invention, the terms "walking stick" and "cane" are used interchangeably and indicate an elongated device used as a walking aid that is gripped by a user. The term "walking stick" also encompasses such collapsible or non-collapsible supports as ski poles, paddles, shovels, tent poles, etc.

For the purposes of the present invention, the term "handle" refers to any device that allows a user to rest the user's weight on one end of the adjustable support of the present invention. Handles of the present invention include: walking stick grips, cane handles, crutch armpit rests, etc. The handles of the present invention may be padded or unpadded.

Unless specified or shown otherwise, for the purposes of the present invention, the term "distal end" refers to the end of an adjustable support from which an inner member of the adjustable support extends or from which an adjustable securing device extends. The other end of the adjustable support is referred to as the "proximal end".

For the purposes of the present invention, the term "longitudinal" refers to a direction along the length of an adjustable support from either the proximal end to distal end or from the distal end to the proximal end.

For the purposes of the present invention, the term "opposed openings" refers to a pair of corresponding openings on opposite sides of a member.

For the purposes of the present invention, the term "cord" refers to any type of cord, natural or synthetic rope, line, chain, etc. that can be used with a pulley of the present invention. When used as part of an adjustment device of the present invention, toe cord is preferably flexible yet sufficiently strong to resist tearing or breaking while passing over pulley posts and moving inner and middle members relative to one another. Although a rope is used as the cord in the embodiments shown in the drawing figures and described below, it should be understood that various kinds of cords can be used in place of the rope of these embodiments.

For the purposes of the present invention, the term "pulley" refers to one or more surfaces, one or more posts, one or more wheels, etc. over which, around which, or through which a cord of the present invention travels to provide a user of a traction splint of the present invention with a mechanical advantage. For the purposes of the present invention, the term "pulley system" refers to the combination of the cord and all of the pulleys in a particular adjustable support of the present invention. Utilizing multiple wheels as pulleys in a pulley system of the present invention allows the user to increase the mechanical advantage of a traction splint of the present invention.

For the purposes of the present invention, the term "limb" refers to any part of a person's leg, including: the foot, ankle, knee, hip, etc. and any part of a person's arm, including: the shoulder, elbow, wrist, hand, etc. The term "limb" may also refer to any part of an individual which may be braced by an adjustable support of the present invention such as an individual's back, neck, etc.

For the purposes of the present invention, the phrase "securing an adjustable support to a limb" refers not only to directly securing the adjustable support of the present invention to an individual's limb, but also to securing the clothing or other objects adjacent to, surrounding or attached to an individual's limb. For example, the adjustable support of the present invention may be secured to an individual's sleeve, pant's leg, sock, shoe, thigh pad, leg wrap, etc.

For the purposes of the present invention, the term "analog adjustment device" refers to a device that may increase or decrease the length of the adjustable support of the present invention by a wide variety of different increments. For example, the pulley system illustrated in the embodiment of FIG. 3A below is such an analog adjustment device. The pulley system allows the length of the adjustable support to be extended by very small, almost continuous increments. In contrast, the term "discrete adjustment device" refers to devices which adjust the length of the adjustable support of the present invention by particular set amounts. For example, both adjustment devices described in the embodiment illustrated in FIG. 1A are "discrete adjustment devices". In these two adjustment devices, the spacing of the holes or slots determines the increments by which the adjustable support's length may be extended.

For the purposes of the present invention, the terms "coarse adjustment" and "fine adjustment" are relative. For a particular adjustable support of the present invention, a course adjustment device adjusts the length of an adjustable support by an increment larger than the increment that the fine adjustment device adjusts the length of the adjustable support.

For the purposes of the present invention, the term "eyelet" refers to a screw with a closed loop at the terminal end. An eyelet is useful for securing a removable strip to the end of the adjustable support.

Figure 1B:
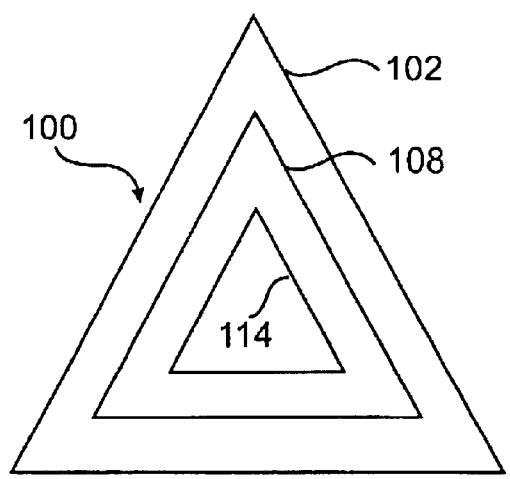
FIG. 1B is a schematic cross-sectional view of the embodiment of FIG. 1A.
Figure 1C:
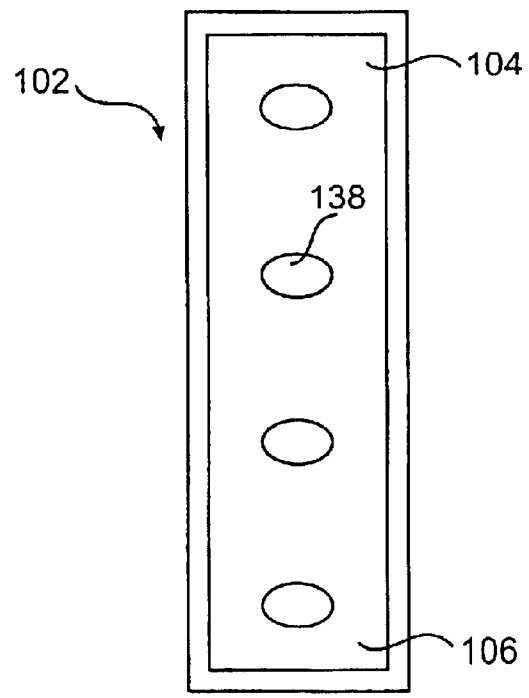
FIG. 1C is a schematic side view of an outer member of the embodiment of FIG. 1A.

For the purposes of the present invention, the term "selectively engaging" refers to a plunger, rod, etc. extending into or through one or more openings that are aligned with the plunger, rod, etc. when two or more of the members of the adjustable support of present invention are in given relationship with one another. For example, in an adjustable support such as that shown in FIGS. 1A and 1B, a plunger on the middle member may selectively engage the first, second, or third opening from the distal end of the outer member, depending on the position of the outer member relative to the middle member.

For the purposes of the present invention, the term "attached" when referring to a cord of the present invention being attached to a member of an adjustable support of the present invention refers to a variety of conventional methods of attachment of one end of a cord to a member. For example, when the cord of the present invention is a rope, a rope can be attached to member threading one end of a rope through a hole in the member and knotting the rope so that the end of the rope cannot pass back through the hole. A rope can also be attached with an adhesive, cleat, Velcro®, staple, etc. or other conventional means for fixing a rope to a member. What is important is that when a cord of the present invention is attached to a member, the attached end of the cord is held or eventually prevented from moving any further, such as by a knot being prevented from going through a hole, when a user pulls on the free end of the cord.

For the purposes of the present invention, the term "constriction loop" refers to an adjustable loop that is used to secure a member of a splint of the present invention to a limb of an individual. A constriction loop is adjustable on the sense that the diameter of a constriction loop can be adjusted to fit the diameter of one of the portions of the limb to which the adjustable support of the present invention is secured. A constriction loop can be formed by twisting an adjustable cord of the present invention or may be a separate loop mounted on an adjustable cord of the present invention. A constriction loop may be constructed from rope, Velcro®, cloth, etc.

Description

FIGS. 1A, 1B, 1C, 1D, and 1E illustrate one embodiment of the adjustable support of the present invention for use as a traction splint. A three-member splint 100 includes an outer member 102 having an outer member distal end 104 and an outer member proximal end 106. Located inside outer member 102 is a middle member 108 having a middle member distal end 110 and a middle member proximal end 112. Located inside middle member 108 is an inner member 114 having an inner member distal end 116 and an inner member proximal end 118 (visible in FIG. 1E). A distal securing device 120 is mounted at inner member distal end 116, and a proximal securing device 130 is mounted at outer member proximal end 106. Distal securing device 120 and proximal securing device 130 allow three-member splint 100 to be secured to an individual (not shown).

In the embodiment shown in FIGS. 1A through 1E, the distal securing device and proximal securing device are shown as rings that could receive a rope, hook and loop fastener, or any other appropriate means of attaching the splint of the present invention to the individual. The distal securing device and the proximal securing device can be fixed or removably attached, and could be of any variety of sizes and shapes as desired for a particular use.

While the members shown in the embodiment of FIGS. 1A through 1E are triangular in cross-section, it is contemplated that the members could be circular, oval, square, rectangular, or other shape in cross-section.

Three-member splint 100 includes a coarse adjustment device 136. Coarse adjustment device 136 consists of a series of circular holes 138 and a spring loaded plunger 142 (only a portion of which is visible in FIG. 1A). Although there are three holes depicted, the number can vary depending on the particular use. Spring loaded plunger 142 is mounted on middle member 108 and is designed to engage any one of holes 138. Only one of holes 138 may be engaged at any time, and plunger 142 must be actively depressed to disengage plunger 142 from one of holes 138. Once plunger 142 is disengaged, middle member 108 and plunger 142 can be moved along the inside of outer member 102 until desired one of holes 126 is engaged as shown in FIG. 1A. Using the procedure just described, coarse adjustment device 136 is able to fix the location of middle member 108 relative to outer member 102 and provides coarse adjustment of splint length $L_1$.

Although the holes and corresponding plunger of the coarse adjustment device are depicted as circular in the embodiment shown in FIGS. 1A through 1E, other shapes such as oval, triangular, square, etc. may be used in the splint of the present invention. Also, the coarse adjustment device may consist of a pair of opposing holes through which a screw, bolt etc. may extend to fix the position of middle member relative to outer member.

Three-member splint 100 also includes a fine adjustment device 144. Fine adjustment device 144 consists of a plurality of slots or openings 146 on an inner member first side 148 that are engaged by a ratchet 152. A ratchet handle 154 allows a user (not shown) to manipulate ratchet 152. When not in use, ratchet handle 154 is stored on middle member 108 as depicted in FIG. 1D. A brake 156 for fine adjustment device 144 consists of a brake distal end 158, a brake middle portion 160, a brake proximal end 162, a spring or brake resistance device 164, and a brake pivot 166. Brake proximal end 162 can be depressed by a user (not shown) to disengage brake 156. Brake distal end 158 is configured to engage openings 168 on a second side of inner member 150 by brake resistance device 164 located between brake proximal end 162 and middle member distal end 110. Inner member distal end 116 is free to move in a distal direction away from middle member distal end 110 when brake 156 is in use. However, openings 168 will engage brake distal end 158 and thereby stop inner member distal end 116 as inner member distal end 116 travels toward middle member distal end 110. Brake pivot 166 allows the use of brake resistance device 164 to encourage brake distal end 158 to engage inner member 114. Fine adjustment device 144 restrains movement of middle member 108 relative to inner member 114 and provides fine adjustment of splint length $L_1$.

The ratchet, brake, and slots of the fine adjustment device of the present invention can vary in size and distribution to change the degree of fine adjustment desired. The ratchet handle may be adapted to be stored on the middle member s shown in FIG. 1D.

The combination of coarse and fine adjustments shown in the embodiment of FIGS. 1A through 1E allow the splint to apply precise and tight traction and may be used to reduce fractures or dislocated joints. Furthermore, the compact design allows the splint to be portable. A portable splint can be used by backpackers as well as all types of emergency medical personnel. The splint of the present invention can also be utilized for injuries to the upper and lower extremities.

Figure 2A:
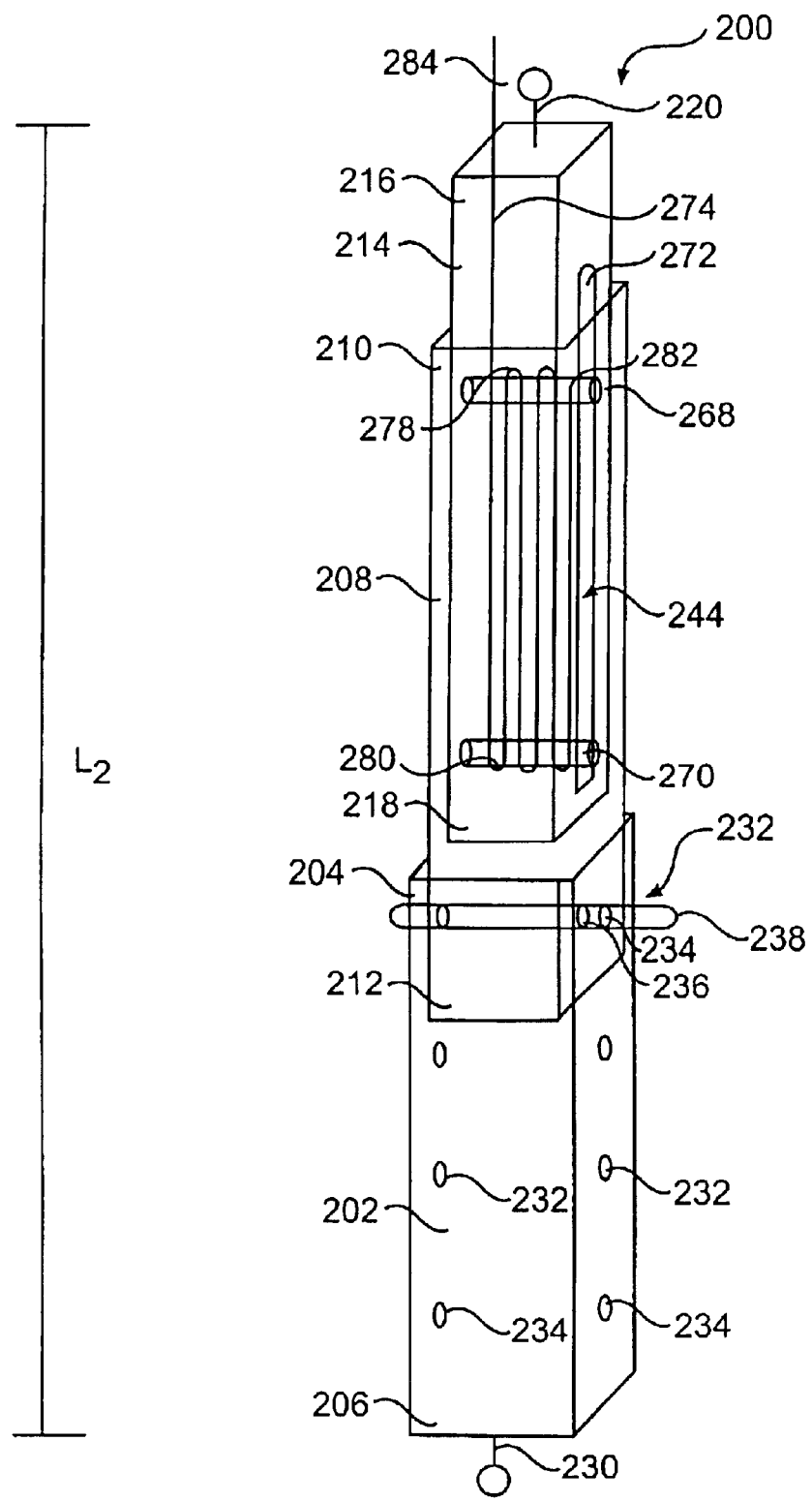
FIG. 2A is a schematic perspective view of another embodiment of an adjustable support of the present invention useful as a traction splint.
Figure 2B:
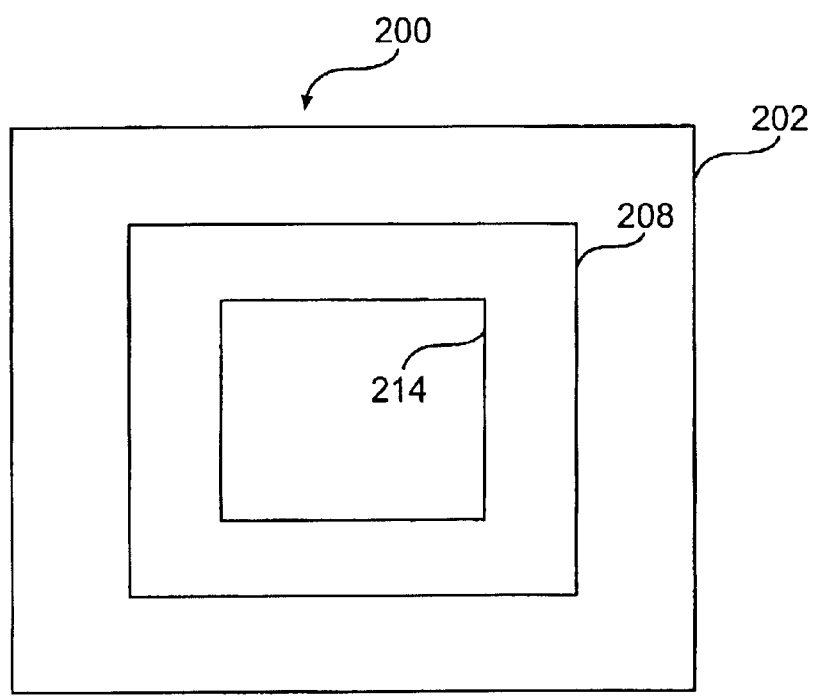
FIG. 2B is a schematic cross-sectional view of the embodiment of FIG. 2A.

FIGS. 2A and 2B illustrate another preferred embodiment of the adjustable support of the present invention that is useful as a traction splint. A three-member splint 200 includes an outer member 202 having an outer member distal end 204 and an outer member proximal end 206. Located inside outer member 202 is a middle member 208 having a middle member distal end 210 and a middle member proximal end 212. Located inside middle member 208 is an inner member 214 having an inner member distal end 216 and an inner member proximal end 218. A distal securing device 220 is mounted at inner member distal end 216, and a proximal securing device 230 is mounted at outer member proximal end 206. Distal securing device 220 and proximal securing device 230 allow three-member splint 200 to be secured to an individual (not shown).

Although for convenience the members of the splint shown in FIGS. 2A and 2B are made of a translucent or transparent plastic material, the materials used to form the traction splint of the present invention may be solid materials as shown in the embodiment of FIGS. 1A through 1E.

In the embodiment shown in FIGS. 2A and 2B, the distal securing device and the proximal securing device are shown as rings that may receive a rope, hook and loop fastener, or any other appropriate means of attaching the splint of the present invention to the individual. The distal securing device and the proximal securing device may be fixed or removably attached, and may be of any variety of sizes and shapes as desired for a particular use.

While the members shown in the embodiment of FIGS. 2A and 2B are square in cross-section, it is contemplated that the members of the splint of the present invention can be circular, oval, triangular, rectangular, or other shape in cross-section.

Three-member splint 200 includes a coarse adjustment device 232. Coarse adjustment device 232 consists of a series of pairs of longitudinally aligned holes 234 in outer member 202, a pair of opposed holes 236 in middle member 208, and a removable locking post 238 which is inserted through holes 236 and a selected pair of holes 234 to fix the position of middle member 208 relative to outer member 202, thereby providing coarse adjustment of splint length $L_2$.

Although the holes and removable locking post of the coarse adjustment device are depicted as circular, other shapes such as oval, triangular, square, etc. may be used in the traction splint of the present invention. Also, the locking post could be replaced with a nail, screw, etc. A flattened end on one or both ends of locking post may be desirable to maintain locking post in a fixed position once the desired series of holes are engaged.

A fine adjustment device 244 is also provided for three-member splint 200. Fine adjustment device 244 is comprised of a distal pulley post 268, a proximal pulley post 270, a pair of openings or slots 272 in inner member 214, and a rope 274. Proximal pulley post 270 is mounted on the inside of inner member 214, and distal pulley post 268 is mounted on the inside of middle member 208. Loops 278 and 280 of rope 274 wrap around distal pulley post 268 and proximal pulley post 270, respectively and rope 274 is attached to pulley post 268 at an attached end 282 of rope 274. Openings 272 in inner member 214 allow for movement of inner member 214 relative to middle member 208 without inner member 214 contacting distal pulley post 268. A user of three-member splint 200 may pull on free end 284 of rope 274 to cause loops 278 and 280, respectively, to tighten and pull distal pulley post 268 and proximal pulley post 270 toward one another. Fine adjustment device 244 allows for movement of inner member 214 relative to middle member 208 and provides fine adjustment of splint length $L_2$. Fine adjustment device 244 also provides mechanical advantage. This allows three-member splint 200 to be used to reduce fractures or dislocations without requiring great strength or exertion by the user.

The a end of the rope used to finely adjust the splint of the present invention may be secured to either pulley post, to either inner or middle member, or to any other suitable location on the splint.

Figure 3A:
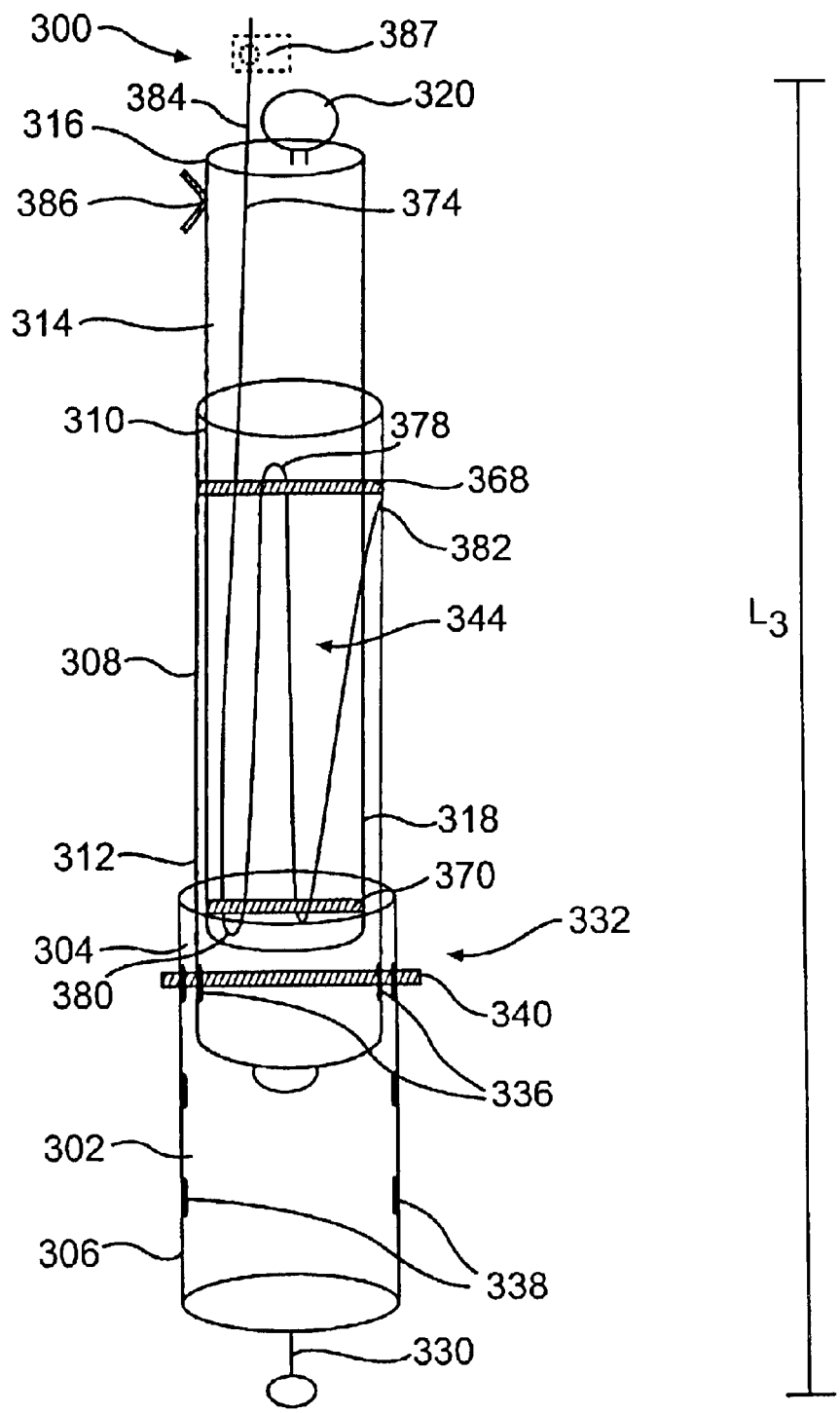
FIG. 3A is a schematic perspective view of another embodiment of an adjustable support of the present invention useful as a traction splint.
Figure 3B:
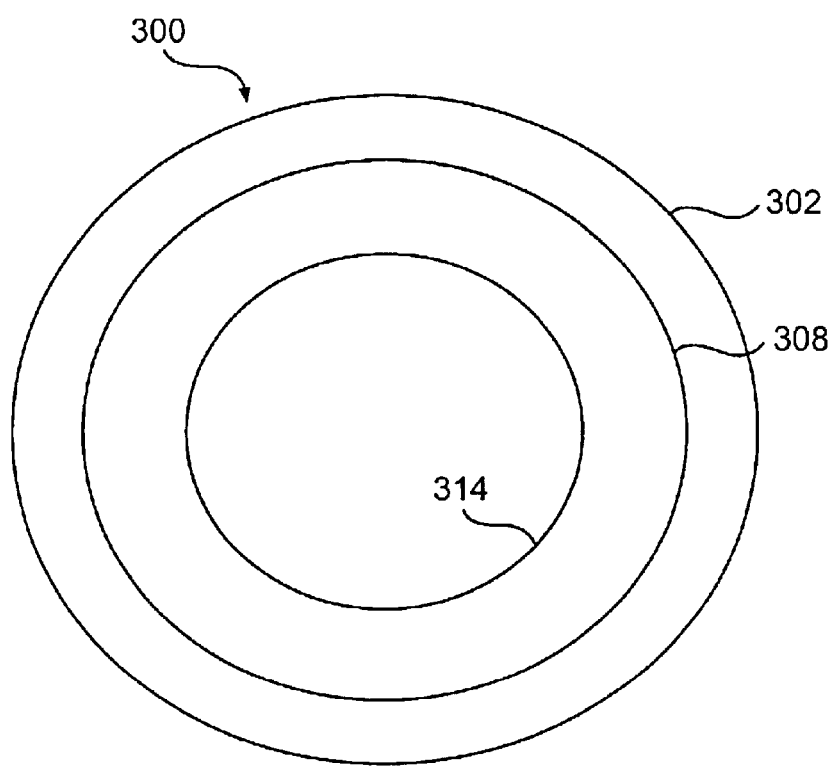
FIG. 3B is a schematic cross-sectional view of the embodiment of FIG. 3A.

FIGS. 3A and 3B illustrate another referred embodiment of the adjustable support of the present invention that is useful as a traction splint. A three-member splint 300 includes an outer member 302 having an outer member distal end 304 and an outer member proximal end 306. Located inside outer member 302 is a middle member 308 having a middle member distal end 310 and a middle member proximal end 312. Located inside middle member 308 is an inner member 314 having an inner member distal end 316 and an inner member proximal end 318. A distal securing device 320 is mounted at inner member distal end 316, and a proximal securing device 330 is mounted at outer member proximal end 306. Distal securing device 320 and proximal securing device 330 allow splint 300 to be secured to an individual (not shown).

In the embodiment shown in FIGS. 3A and 3B, the distal securing device and the proximal securing device are shown as rings that can receive a rope, hook and loop fastener, or any other appropriate means of attaching the splint of the present invention to an individual. The distal securing device and the proximal securing device can be fixed or removably attached, and can be of any variety of sizes and shapes as desired for a particular use.

While the members of the splint shown in the embodiment of FIGS. 3A and 3B are circular in cross-section, it is contemplated that the members can be, oval, triangular, square, rectangular, or other shape in cross-section.

Three-member splint 300 includes a coarse adjustment device 332. Coarse adjustment device 332 consists of a series of pairs of longitudinally aligned holes 338 in outer member 302, a pair of opposed holes 336 in middle member 308, and a removable locking post 340 which is inserted through holes 336 and a selected pair of holes 338 to fix the position of middle member 308 relative to outer member 302, thereby providing coarse adjustment of splint length $L_3$.

Although the holes and removable locking post of the coarse adjustment device are depicted as circular, other shapes such as oval, triangular, square, etc. may be used in the traction splint of the present invention. Also, the locking post can be replaced with a nail, screw, etc. A flattened end on one or both ends of the locking post may be desirable to maintain the locking post in a fixed position once the desired series of holes is engaged.

A fine adjustment device 344 is also provided for three-member splint 300. Fine adjustment device 344 is comprised of a distal pulley post 368, a proximal pulley post 370, and a rope 374. Distal pulley post 368 is mounted inside middle member 308 and proximal pulley post 370 is mounted to the inside of inner member 314. Loops 378 and 380 of rope 374 wrap around distal pulley post 368 and proximal pulley post 370, respectively and rope 374 is attached at an attached end 382 to middle member 308. Openings in inner member 314 (not shown) allow for movement of inner member 314 relative to middle member 308 without inner member 314 contacting distal pulley post 368. A user of three-member splint 300 may pull on free end 384 of rope 374 to cause loops 378 and 380 of rope 374 around distal pulley post 368 and proximal pulley post 370, respectively, to tighten and pull distal pulley post 368 and proximal pulley post 370 toward one another. Fine adjustment device 344 allows for movement of inner member 314 relative to middle member 308 and provides fine adjustment of splint length $L_3$.

Fine adjustment device 344 also provides mechanical advantage. That allows three-member splint 300 to be used to reduce fractures or dislocations without requiring great strength or exertion by the user. Rope 374 is attached to middle member distal end 310 at attached end 382 of rope 374. Once a desired splint length $L_3$ is achieved, free end 384 of rope 374 can be secured at a cleat 386. Fine adjustment device 344 allows inner member 314 to be moved relative to middle member 308 and allows fine adjustment of splint length $L_3$.

The fine adjustment device of the splint of FIGS. 3A and 3B provides mechanical advantage. Mechanical advantage allows the splint to reduce fractures or dislocations without great strength or exertion by the user. The cleat is shown at the inner member distal end, but other locations on or in the splint may be utilized. The cleat may be a conventional cleat, a hook, or other suitable fastener for securing the rope. Other methods for fastening rope, represented by dotted device 387, include the use of a spring loaded block similar to the drawstring stopper common on outerwear to prevent passage of rope into distal end 316 of inner member 314. Alternative means to prevent rope passage are tying a knot, or utilizing any other device slidable along the cord holding the cord in position at length.

FIGS. 4A and 4B illustrate another preferred embodiment of the adjustable support of the present invention that is useful as a traction splint. A two-member splint 400 includes an outer member 402 having an outer member distal end 404 and an outer member proximal end 406. Located inside outer member 402 is an inner member 414 having an inner member distal end 416 and an inner member proximal end 418. A distal securing device 420 is mounted at inner member distal end 416, and a proximal securing device 430 is mounted at outer member proximal end 406. Distal securing device 420 and proximal securing device 430 attach two-member splint 400 to an individual (not shown).

In the embodiment shown in FIGS. 4A and 4B, the distal securing device and the proximal securing device are shown as rings that can receive a rope, hook and loop fastener, or any other appropriate means of attaching the splint of the present invention to the individual. The distal securing device and the proximal securing device can be fixed or removably attached, and can be of any variety of sizes and shapes as desired for a particular use An adjustment device 444 is also provided for two-member splint 400. Adjustment device 444 is comprised of a distal pulley post 468, a proximal pulley post 470, a pair of openings 472 in inner member 414, and a rope 474. Proximal pulley post 470 is mounted to the inside of inner member 414, and distal pulley post 468 is mounted to the inside of inner member 402. Loops 478 and 480 of rope wrap around distal pulley post 468 and proximal pulley post 470, respectively. Openings 472 in inner member 414 allow for movement of inner member 414 relative to outer member 402 without inner member 414 contacting distal pulley post 468. A user of two-member splint 400 can pull on the free end 484 of rope to cause loops 478 and 480 of rope 474 around distal pulley post 468 and proximal pulley post 470, respectively, to tighten and pull distal pulley post 468 and proximal pulley post 470 toward one another. Fine adjustment device 444 allows for movement of inner member 414 relative to outer member 402 and provides fine adjustment of splint length $L_4$. Fine adjustment device 444 also provides mechanical advantage. That allows two member splint 400 to be used to reduce fractures or dislocations without great strength or exertion by the user. Rope 474 is attached to outer member distal end 404 at a attached end 482 of rope 474. Once a desired splint length $L_4$ is achieved, free end 484 of rope 474 can be secured at a cleat 486. Fine adjustment device 444 allows inner member 414 to be moved relative to outer member 402 and provides fine adjustment of splint length $L_4$.

The rope locking point is shown along the inner member distal end, but other locations on or in the splint may be utilized. The rope locking point may be comprised of a hook, cleat, or other suitable fastener for securing the rope. Other methods for locking the rope in position are tying a knot on the rope, or using a slidable device to engage the rope and restrict motion toward the splint, thereby maintaining traction.

Figure 5:
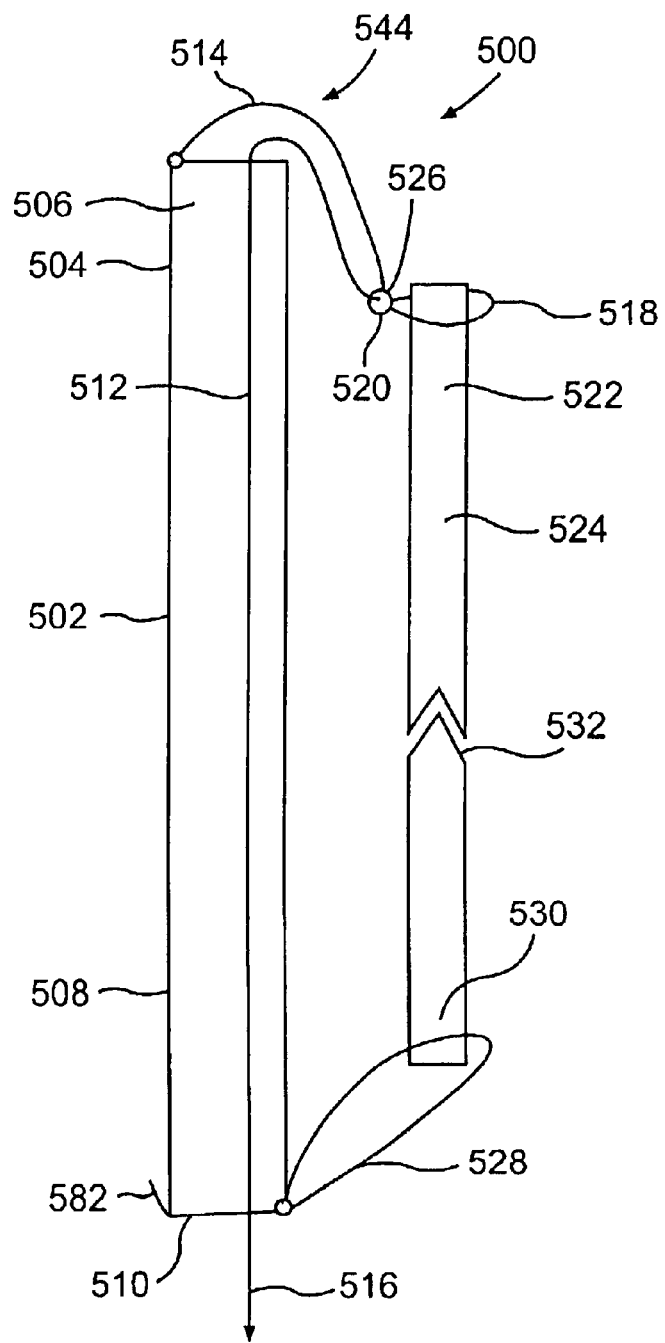
FIG. 5 is a schematic front view of another embodiment of an adjustable support of the present invention useful as a traction splint.

FIG. 5 illustrates a fifth embodiment of the present invention. A single-member splint 500 includes a hollow member 502 having a member distal end 504 having an opening 506 and a member proximal end 508 having an opening 510. A rope 512 extends through hollow member 502 and includes a rope distal end 514 which extends from member distal end 504 and a free rope end 516 that extends from member proximal end 508. Constriction loop 518 is used to secure single-member splint 500 to a first end 522 of an individual's limb 524 (shown schematically for simplicity of illustration) by looping constriction loop 518 around first end 522 and using a ring connection device 526 to attach to rope 512. A proximal securing loop 528 is attached to member proximal end 508 and is looped around a second end 530 of limb 524. By pulling on free rope end 516, first end 522 and second end 530 of limb 524 are pulled away form each other, straightening limb 524 and taking pressure off a fracture 532 in limb 524.

Although in FIG. 5, the traction splint of the present invention is shown for use in treating a fracture, the traction splint of the present invention may also be used to provide traction to other kinds of injuries and separations, such as dislocations.

The distal end of the rope is preferably attached to the distal end of the member as depicted in FIG. 5, but can also be located at another location on or in the member. The rope can be fixed or removably attached to the member. The proximal securing loop is preferably attached to the proximal end of the member as shown in FIG. 5, but could be located somewhat away from the proximal end. Instead of being a piece of rope, the proximal securing loop and distal constriction loop can be made of fabric, Velcro®, etc.

Proximity between the member distal end and the point distal to the fracture is desirable, as well as the rope loop fitting snugly around the point to the fracture being secured. Although shown as a ring, the constriction device for the splint shown in FIG. 5 can be any suitable device that allows for rope movement. The length, relative straightness, and stability provided by the hollow member of the splint combined with a steady pull on the rope by a user contribute to a smooth straight motion of the point distal to the fracture away from the fracture, thereby reducing or securing the fracture and possibly alleviating some discomfort felt by the individual.

The hollow member shown in FIG. 5 can be circular, oval, triangular, square, rectangular, or other shape in cross-section as desired. The ratio of length to width of the hollow member can be various chosen ratios. Although the fifth embodiment of the present invention describes a hollow tube as the member, it is contemplated that a solid or otherwise not consistently hollow device could form a portion of the member. The member preferably has a hollow portion which allows the rope to pass through, but it is not necessary that the entire member be hollow. Also, the hollow portion of the member need not be of consistent diameter through the length of the tube, or centered, as shown in the embodiment of FIG. 5.

In choosing a member for the splint for a particular application, it is important to consider the number of coils of rope to be contained therein and the diameter of the rope to be employed. A suitably sized member can allow for ease of movement of the rope loops within the member but still be compact enough to be readily transportable.

Fine adjustment device provides mechanical advantage. Mechanical advantage allows splint to reduce fractures or dislocations without great strength or exertion by the user. The rope locking point is shown along proximal end of inner member, but other locations on or in the splint may be utilized. Rope locking point may be comprised of a hook, cleat, or other suitable fastener for securing the rope.

Distal securing device and proximal securing device are shown as a strip of hook and pile fastening material that could be wrapped around a limb to attach adjustable support to an individual. Distal securing device and proximal securing device could be fixed or removable, and could be of any variety of sizes and shapes as desired.

Although the holes and corresponding plunger of the coarse adjustment device are depicted as circular, other shapes such as oval, triangular, square, etc. may be used in the traction splint of the present invention. Also, the plunger could be replaced with a hole through which a nail, screw, etc. may be provided to engage middle member and secure middle member to outer member.

The unique combination of coarse and fine adjustments allows the splint of the present invention to apply precise and tight traction and may be used to reduce fractures or dislocated joints. Furthermore, the compact design allows the splint to be portable. A portable splint may be used by backpackers as well as all types of emergency medical personnel. The design also allows the splint to be utilized for injuries to the upper and lower extremities.

Figure 6:
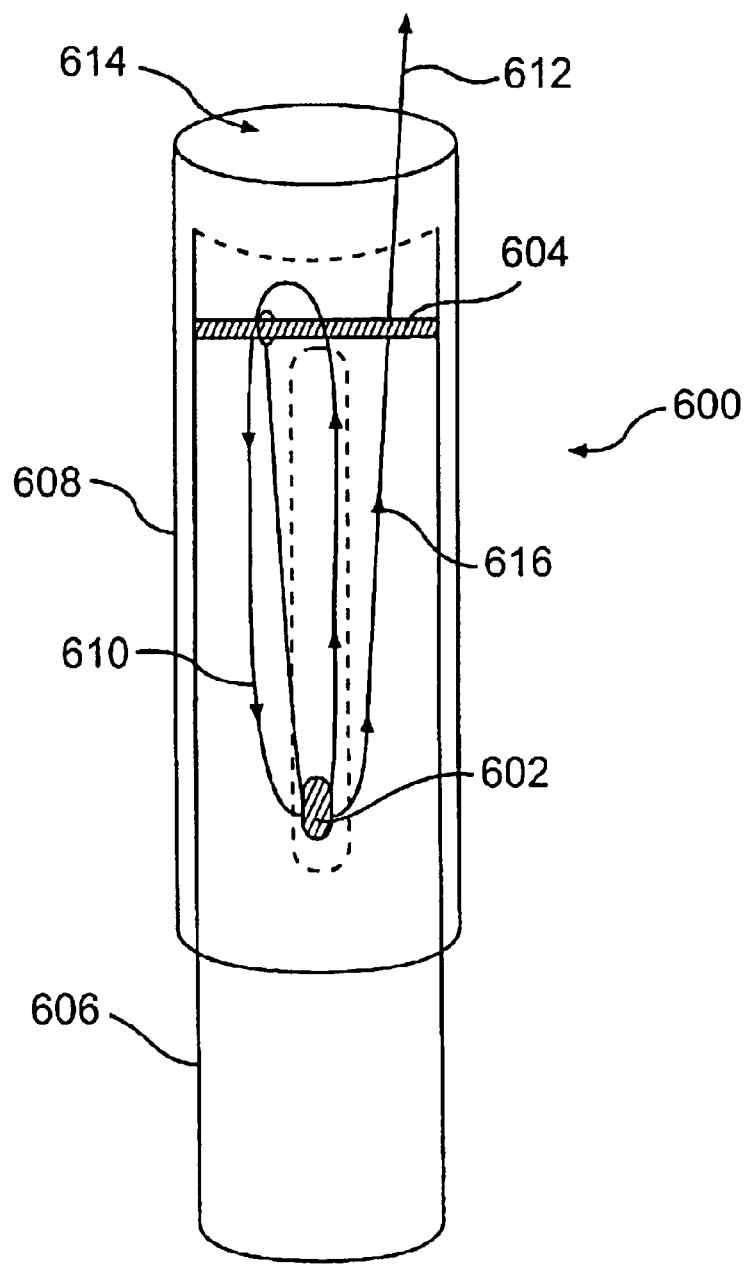
FIG. 6 is a schematic front view of another embodiment of an adjustable support of the present invention.

FIG. 6 illustrates an embodiment of the present invention in which an adjustable support 600 includes a distal pulley post 602 and a proximal pulley post 604 that are offset at an angle 90° with respect to each other, unlike the previously described embodiments in which the distal and proximal pulley posts are in parallel. Distal pulley post 602 is mounted in an outer member 608 and proximal pulley post 604 is mounted in an inner member 606. A cord 610 is attached to proximal pulley post 604, wraps around distal pulley post 602 and proximal pulley post 604 and a free end 612 of cord 610 extends out of an opening 614 in outer member 608. Arrows 616 indicate the direction cord 610 is pulled when a user pulls on free end 612. Such an arrangement of a pulley post and cord may be valuable in providing a particular degree of resistance to adjustment in particular circumstances.

Figure 7:
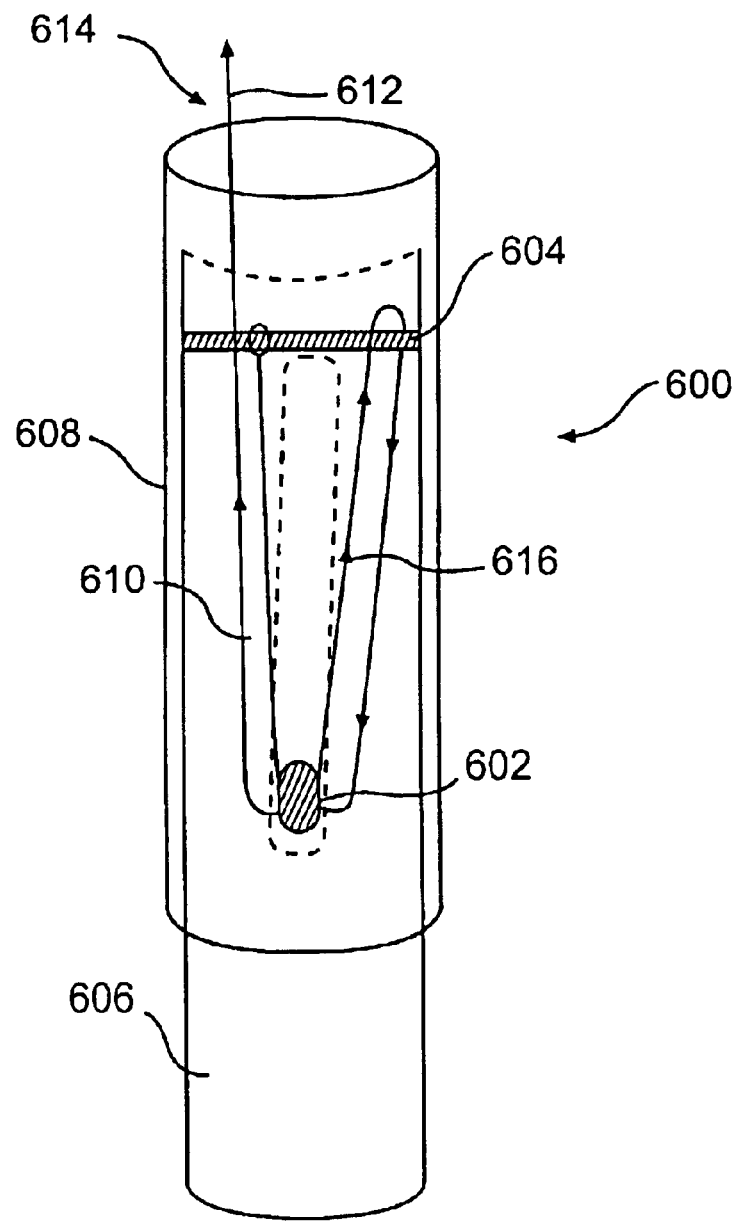
FIG. 7 is a schematic front view of another embodiment of an adjustable support of the present invention.

FIG. 7 illustrates another embodiment of the present invention that differs from the embodiment of FIG. 6 only in how cord 610 is wrapped around proximal pulley post 604 and distal pulley post 602.

Figure 8:
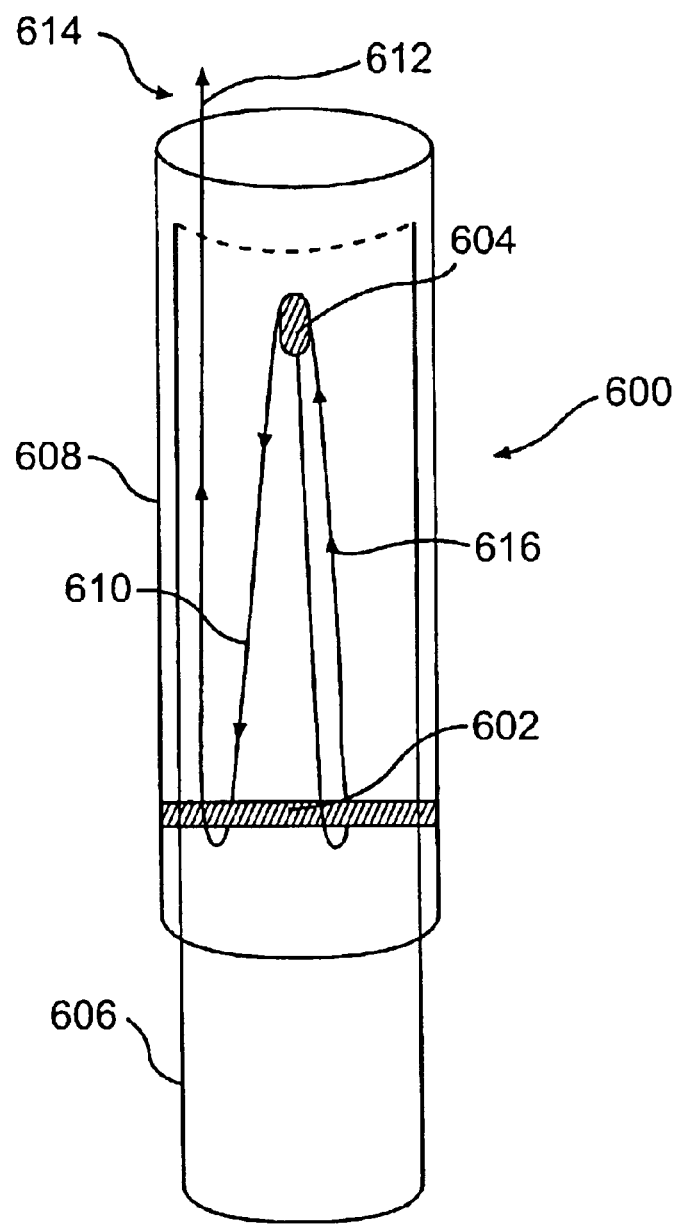
FIG. 8 is a schematic front view of another embodiment of an adjustable support of the present invention.

FIG. 8 illustrates another embodiment of the present invention that differs from the embodiments of FIG. 6 and FIG. 7 only in how cord 610 is wrapped around proximal pulley post 604 and distal pulley post 602.

As illustrated by FIGS. 6, 7 and 8, a given adjustable support of the present invention, may have various cord wrapping arrangements.

Figure 9:
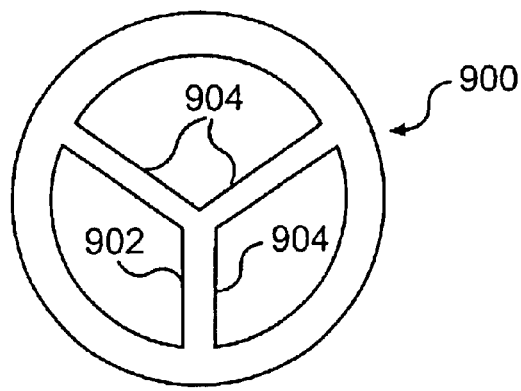
FIG. 9 is a cross-sectional view of a member of another embodiment of an adjustable support of the present invention.
Figure 10:
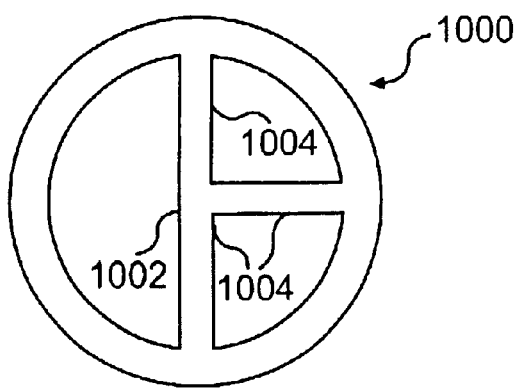
FIG. 10 is a cross-sectional view of a member of another embodiment of an adjustable support of the present invention.
Figure 11:
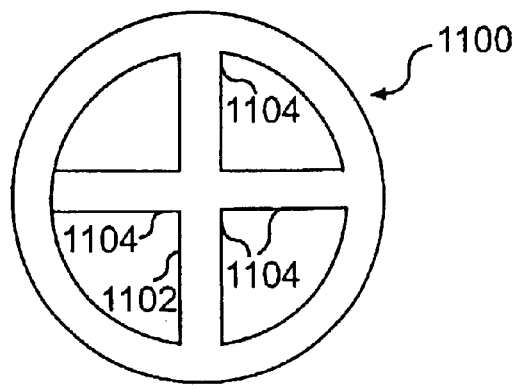
FIG. 11 is a cross-sectional view of a member of another embodiment of an adjustable support of the present invention.

Although FIGS. 6, 7 and 8 illustrate an adjustable support of the present invention in which the distal pulley post and proximal pulley posts are offset an angle of 90° with respect to each other, the distal pulley post and proximal pulley posts of the present invention may be offset at other angles as well and may be multi-pronged. For example, FIG. 9 illustrates an adjustable support 900 of the present invention having a three-pronged pulley post 902 with three prongs 904, FIG. 10 illustrates another adjustable support 1000 of the present invention having a three-pronged pulley post 1002 with three prongs 1004, and FIG. 11 illustrates an adjustable support 1100 having a four-pronged pulley post 1102 with three prongs 1104.

Figure 12:
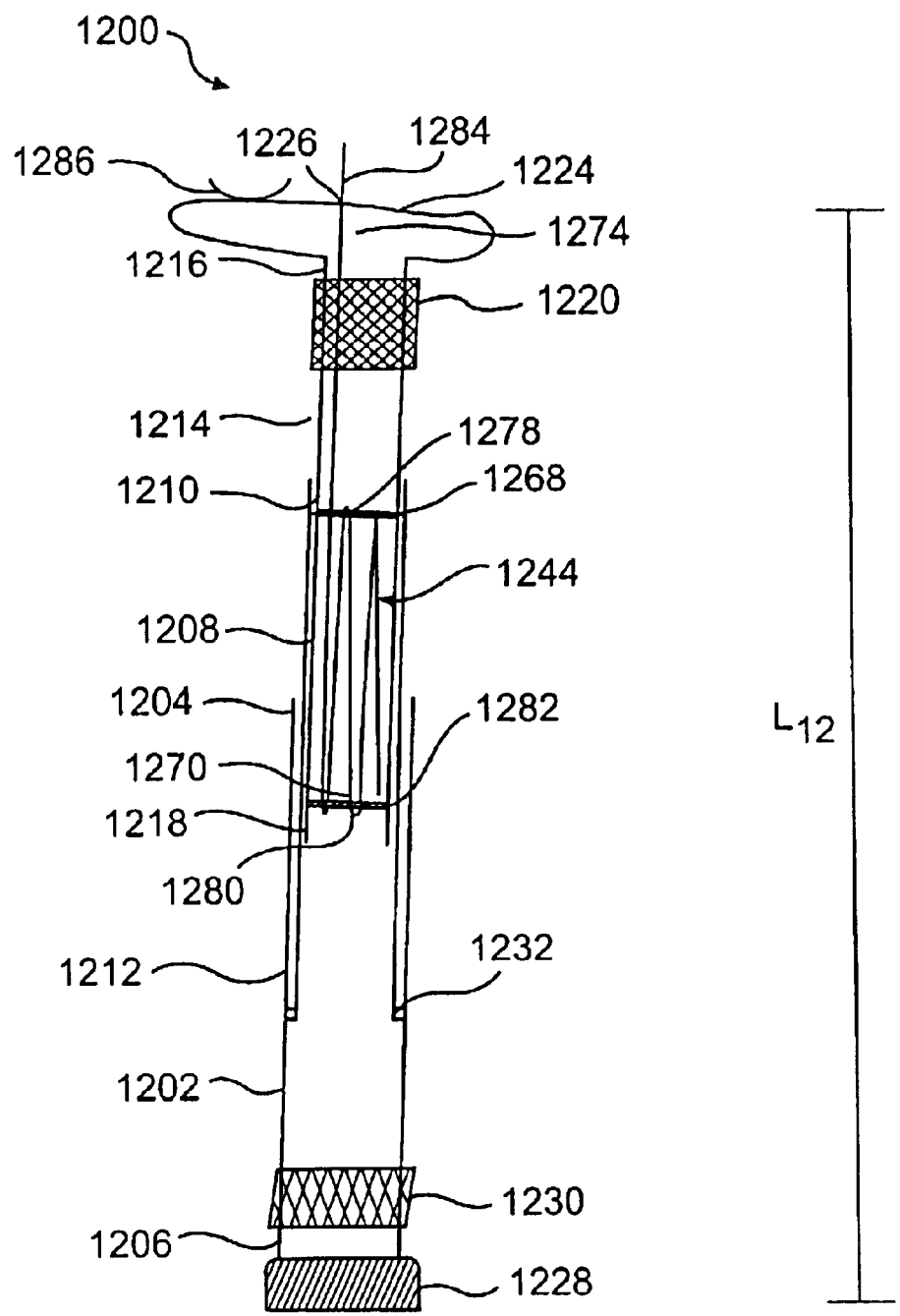
FIG. 12 is a schematic front view of another embodiment of an adjustable support of the present invention useful as a walking stick or crutch.

FIG. 12 illustrates a preferred embodiment of the adjustable support of the present invention that is useful as a walking stick or crutch, depending on the length of the members of the adjustable support. A three-member adjustable support 1200 includes an outer member 1202 having an outer member distal end 1204 and an outer member proximal end 1206. Located inside outer member 1202 is a middle member 1208 having a middle member distal end 1210 and a middle member proximal end 1212. Located inside middle member 1208 is an inner member 1214 having an inner member distal end 1216 and an inner member proximal end 1218. A distal securing device 1220 is mounted at inner member distal end 1216, and a proximal securing device 1222 is mounted at outer member proximal end 1206. Distal securing device 1220 and proximal securing device 1222 allow three-member adjustable support 1200 to be secured to an individual (not shown). Mounted on inner member distal end 1210 is a handle 1224 that may either be gripped by a user as a walking stick or may fit under a user's armpit as a crutch. Handle 1224 also includes an opening 1226. Mounted on outer member proximal end 1206 is a conventional resilient base 1228, such as a rubber base, of the type commonly found on the ends of crutches or canes.

Although the proximal securing device and distal securing device shown in FIG. 12 are Velcro® straps, other conventional securing devices may also be used with the walking stick or crutch of the present invention. For example, the distal securing device and the proximal securing device may be eyelets that could receive a rope, hook and loop fastener, or any other appropriate means of attaching the adjustable support to an individual. The distal securing device could be the strap of a walking stick or ski pole. The distal securing device and proximal securing device may be fixed or removable, and may be of any variety of sizes and shapes as desired.

While the members of the splint shown in the embodiment of FIG. 12 are circular in cross-section, it is contemplated that the members can be, oval, triangular, square, rectangular, or other shape in cross-section.

The handle for the adjustable support of the present invention may be designed solely for use as a walking stick, solely for use as a crutch, for dual use as a walking stick and as a crutch. In order to be used as a crutch, the adjustable support will need to have a maximum extension long enough to fit under a user's armpit. In order to be used as a walking stick, the adjustable support need only be long enough to allow a user to grip and lean on the adjustable support.

The resilient base of the adjustable support of the present invention may be any conventional resilient base, such as the resilient bases used at the ends of canes, walking sticks, crutches, etc.

As shown in FIG. 12, three-member adjustable support 1200 includes a coarse adjustment device 1232. Coarse adjustment device 1232 is a conventional rotating locking mechanism that may be used to fix the position of middle member 1208 relative to outer member 1202, thereby providing coarse adjustment of adjustable support length $L_{12}$. Coarse adjustment device 1232 operates by rotating middle member 1208 relative to outer member 1202 until middle member 1208 is locked in place relative to outer member 1202. Such conventional rotating locking mechanisms are commonly utilized in telescoping extension poles, such as ski poles or extension poles used in washing windows or pruning trees.

Three-member adjustable support 1200 includes a fine adjustment device 1244. Fine adjustment device 1244 is comprised of a distal pulley post 1268, a proximal pulley post 1270, and a rope 1274 that extends through opening 1226 in handle 1224. Distal pulley post 1268 is mounted inside middle member 1208 and proximal pulley post 1270 is mounted to the inside of inner member 1214. Loops 1278 and 1280 of rope 1274 wrap around distal pulley post 1268 and proximal pulley post 1270, respectively. Rope 1274 is attached to proximal pulley post 1270 at an attached end 1282 of rope 1274. Openings in inner member 1214 (not shown) allow for movement of inner member 1214 relative to middle member 1208 without inner member 1214 contacting distal pulley post 1268. A user of three-member adjustable support 1200 may pull on free end 1284 of rope 1274 to cause loops 1278 and 1280 of rope 1274 around distal pulley post 1268 and proximal pulley post 1270, respectively, to tighten and pull distal pulley post 1268 and proximal pulley post 1270 toward one another. Fine adjustment device 1244 allows for movement of inner member 1214 relative to middle member 1208 and provides fine adjustment of adjustable support length $L_{12}$.

Fine adjustment device 1244 also provides mechanical advantage that allows three-member adjustable support 1200 to be used to reduce fractures or dislocations in limbs secured to three-member adjustable support 1200 without requiring great strength or exertion by the user. Once a desired adjustable support length $L_{12}$ is achieved, free end 1284 can be secured at a cleat 1286 mounted on handle 1224. Fine adjustment device 1244 allows inner member 1214 to be moved relative to middle member 1208 and allows fine adjustment of adjustable support length $L_{12}$.

The cleat of the adjustable support of FIG. 12 is shown at the inner member distal end, but other locations on or in the splint may be utilized. The cleat may be a conventional cleat, a hook, or other suitable fastener for securing the rope. Other methods for locking the rope in position are tying a knot on the rope, or using a slidable device to engage the rope and restrict motion toward the splint, thereby maintaining traction.

Figure 13:
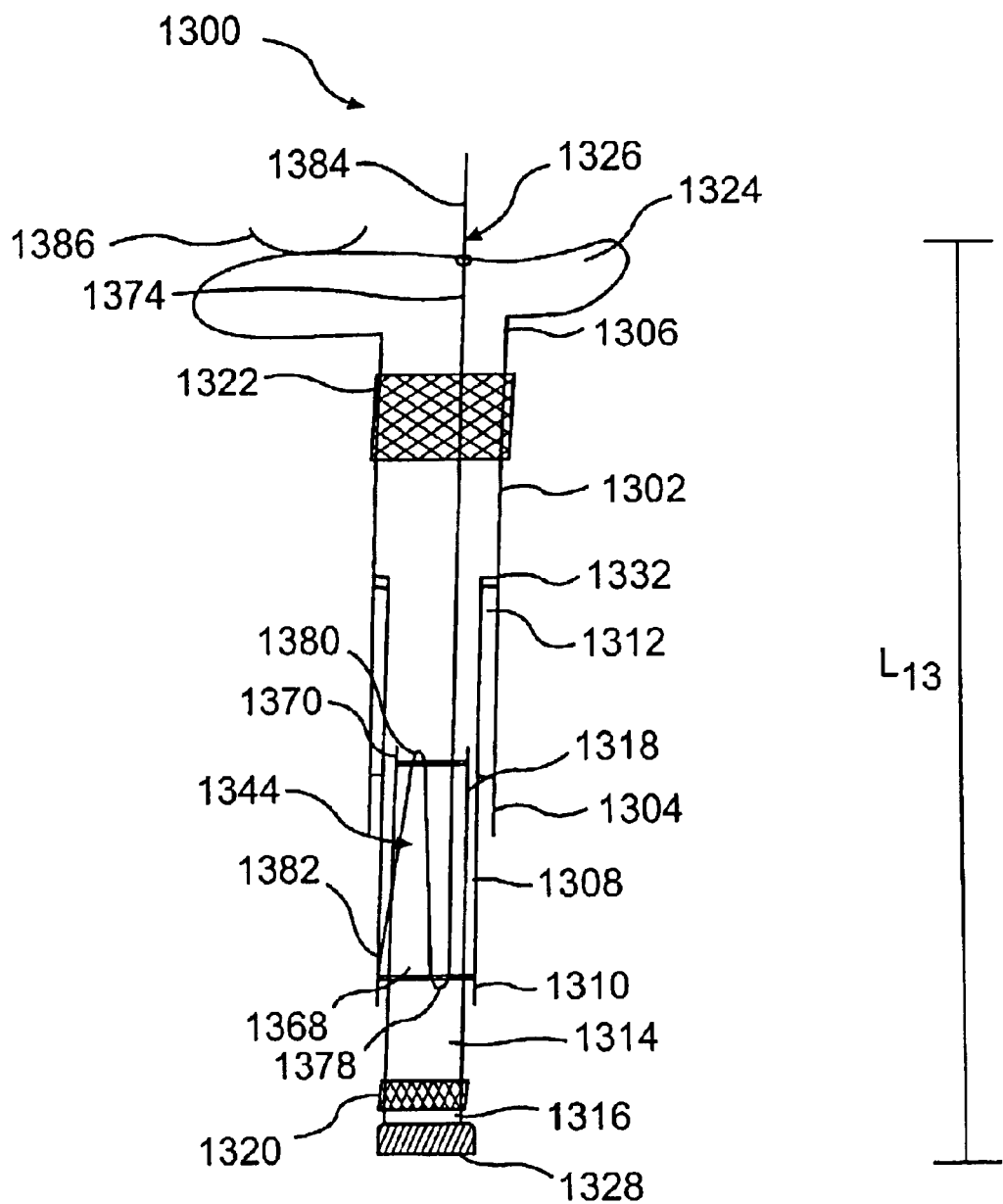
FIG. 13 is a schematic front view of another embodiment of an adjustable support of the present invention useful as a walking stick or crutch.

FIG. 13 illustrates a preferred embodiment of the adjustable support of the present invention that is useful as a walking stick or crutch, depending on the length of the members of the adjustable support. A three-member adjustable support 1300 includes an outer member 1302 having an outer member distal end 1304 and an outer member proximal end 1306. Located inside outer member 1302 is a middle member 1308 having a middle member distal end 1310 and a middle member proximal end 1312. Located inside middle member 1308 is an inner member 1314 having an inner member distal end 1316 and an inner member proximal end 1318. A distal securing device 1320 is mounted at inner member distal end 1316, and a proximal securing device 1322 is mounted at outer member proximal end 1306. Distal securing device 1320 and proximal securing device 1322 allow three-member adjustable support 1300 to be secured to an individual (not shown). Mounted on outer member proximal end 1306 is a handle 1324 that may either be gripped by a user as a walking stick or may fit under a user's armpit as a crutch. When used as a femoral splint, padded handle may be placed between legs as described by Borschneck, U.S. Pat. No. 4,608,971, or to side of injured limb. Handle 1324 also includes an opening 1326. Mounted on inner member distal end 1316 is a conventional resilient base 1328, such as a rubber base, of the type commonly found on the ends of crutches or canes.

Although the proximal securing device and distal securing device shown in FIG. 13 are Velcro® straps, other conventional securing devices may also be used with the walking stick or crutch of the present invention. For example, the distal securing device and the proximal securing device may be eyelets that could receive a rope, hook and loop fastener, or any other appropriate means of attaching the adjustable support to an individual. The distal securing device could be the strap of a walking stick or ski pole. The distal securing device and proximal securing device may be fixed or removable, and may be of any variety of sizes and shapes as desired.

While the members of the splint shown in the embodiment of FIG. 13 are circular in cross-section, it is contemplated that the members can be, oval, triangular, square, rectangular, or other shape in cross-section.

The handle for the adjustable support of the present invention may be designed solely for use as a walking stick, solely for use as a crutch, for dual use as a walking stick and as a crutch. In order to be used as a crutch, the adjustable support will need to have a maximum extension long enough to fit under a user's armpit. In order to be used as a walking stick, the adjustable support need only be long enough to allow a user to grip and lean on the adjustable support.

The resilient base of the adjustable support of the present invention may be any conventional resilient base, such as the resilient bases used at the ends of canes, walking sticks, crutches, etc.

As shown in FIG. 13, three-member adjustable support 1300 includes a coarse adjustment device 1332. Coarse adjustment device 1332 is a conventional rotating locking mechanism that may be used to fix the position of middle member 1308 relative to outer member 1302, thereby providing coarse adjustment of adjustable support length $L_{13}$. Coarse adjustment device 1332 operates by rotating middle member 1308 relative to outer member 1302 until middle member 1308 is locked in place relative to outer member 1302.

Three-member adjustable support 1300 includes a fine adjustment device 1344. Fine adjustment device 1344 is comprised of a distal pulley post 1368, a proximal pulley post 1370, and a rope 1374 that extends through opening 1326 in handle 1324. Distal pulley post 1368 is mounted inside middle member 1308 and proximal pulley post 1370 is mounted to the inside of inner member 1314. Loops 1378 and 1380 of rope 1374 wrap around distal pulley post 1368 and proximal pulley post 1370, respectively. Rope 1374 is attached to middle member 1308 at attached end 1382 of rope 1374. Openings in inner member 1314 (not shown)

allow for movement of inner member 1314 relative to middle member 1308 without inner member 1314 contacting distal pulley post 1368. A user of three-member adjustable support 1300 may pull on free end 1384 of rope 1374 to cause loops 1378 and 1380 of rope 1374 around distal pulley post 1368 and proximal pulley post 1370, respectively, to tighten and pull distal pulley post 1368 and proximal pulley post 1370 toward one another. Fine adjustment device 1344 allows for movement of inner member 1314 relative to middle member 1308 and provides fine adjustment of adjustable support length $L_{13}$.

Fine adjustment device 1344 also provides mechanical advantage that allows three-member adjustable support 1300 to be used to reduce fractures or dislocations in limbs secured to three-member adjustable support 1300 without requiring great strength or exertion by the user. Once a desired adjustable support length $L_{13}$ is achieved, free end 1384 can be secured at a cleat 1386 mounted on handle 1324. Fine adjustment device 1344 allows inner member 1314 to be moved relative to middle member 1308 and allows fine adjustment of adjustable support length $L_{13}$.

The cleat of the adjustable support of FIG. 13 is shown at the outer member proximal end, but other locations on or in the splint may be utilized. The cleat may be a conventional cleat, a hook, or other suitable fastener for securing the rope. Other methods for locking the rope in position are tying a knot on the rope, or using a slidable device to engage the rope and restrict motion toward the splint, thereby maintaining traction.

Figure 14:
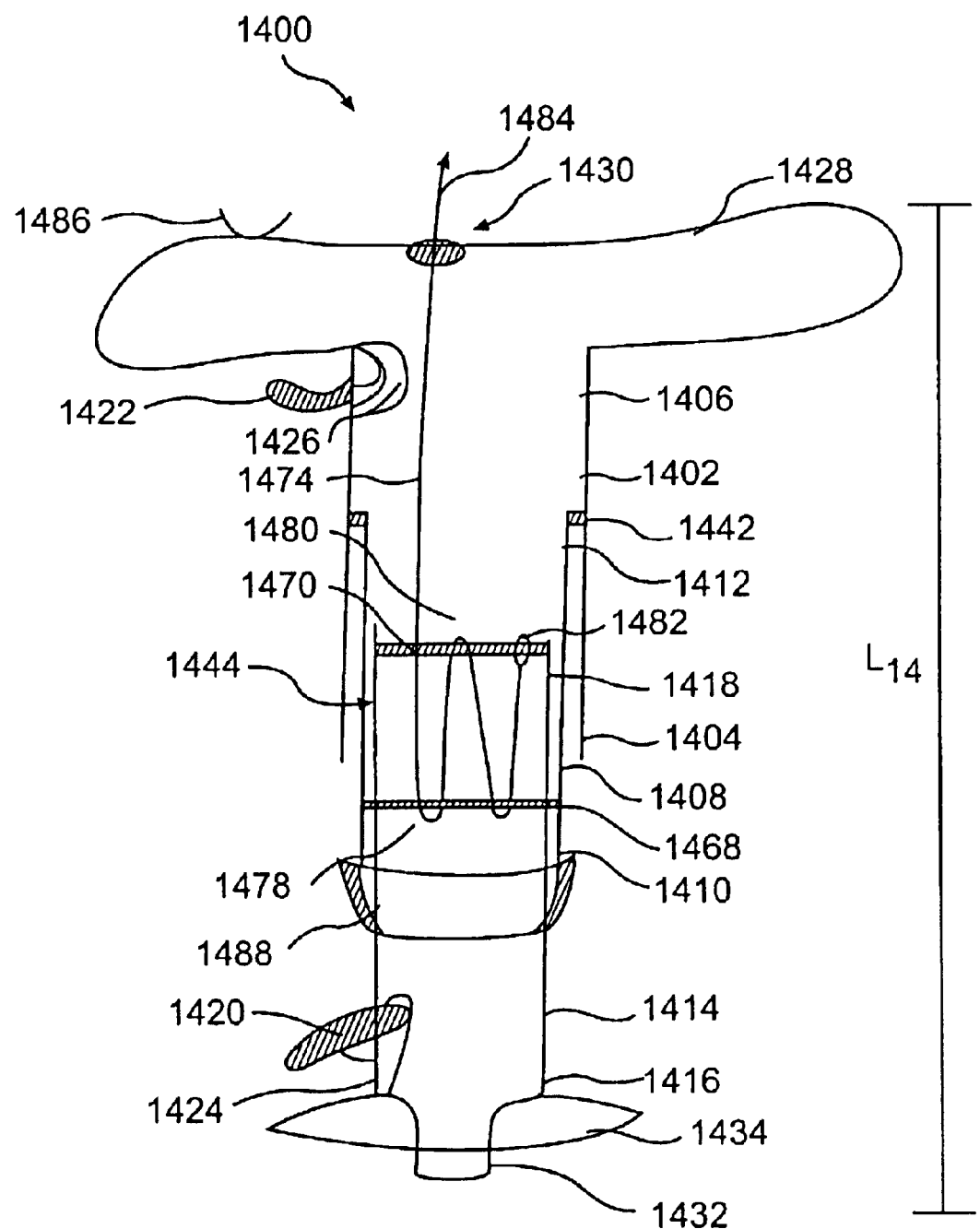
FIG. 14 is a schematic front view of another embodiment of an adjustable support of the present invention useful as a walking stick or crutch.

FIG. 14 illustrates a preferred embodiment of the adjustable support of the present invention that is useful as a walking stick or crutch, depending on the length of the members of the adjustable support. A three-member adjustable support 1400 includes an outer member 1402 having an outer member distal end 1404 and an outer member proximal end 1406. Located inside outer member 1402 is a middle member 1408 having a middle member distal end 1410 and a middle member proximal end 1412. Located inside middle member 1408 is an inner member 1414 having an inner member distal end 1416 and an inner member proximal end 1418. A distal securing device 1420 is mounted at inner member distal end 1416, and a proximal securing device 1422 is mounted at outer member proximal end 1406. Distal securing device 1420 is a retractable hook that is designed to engage a strap (not shown) on the individual's clothing (not shown). Distal securing device 1420 is typically 7 to 10 cm long so that distal securing device 1420 may extend under the sole of the foot of the individual (not shown) and provide a point of even traction. Retracted position 1424 of distal securing device 1420 is shown by shadow lines. Proximal securing device 1422 is a retractable hook for fastening to a strap (not shown) on an individual (not shown). Retracted position 1426 of proximal securing device 1422 is shown by shadow lines. Distal securing device 1420 and proximal securing device 1422 allow three-member adjustable support 1400 to be secured to an individual (not shown). Mounted on outer member proximal end 1406 is a handle 1428 that may either be gripped by a user as a walking stick or may fit under a user's armpit as a crutch. Handle 1428 also includes an opening 1430. Mounted on inner member distal end 1416 is a stopper 1432 made of metal or rubber, the type commonly found on the ends of walking sticks, ski poles, crutches or canes. A basket 1434 is mounted at inner member distal end 1416 proximally of stopper 1432 to prevent three-member adjustable support 1400 from sinking too deeply into mud, soft ground or snow when an individual uses adjustable support 1400 on such terrain or when adjustable support 1400 is used as ski pole. Basket 1434 may also be used instead of 1420 as distal securing device by looping strap over stopper 1432.

Although the proximal securing device and distal securing device shown in FIG. 14 are retractable hooks, Velcro® straps, or other conventional securing devices may also be used with the walking stick or crutch of the present invention. For example, the distal securing device and the proximal securing device may be eyelets that could receive a rope, hook and loop fastener, or any other appropriate means of attaching the adjustable support to an individual. The proximal securing device could be the strap of a walking stick or ski pole. The distal securing device and proximal securing device may be fixed or removable, and may be of any variety of sizes and shapes as desired.

While the members of the splint shown in the embodiment of FIG. 14 are circular in cross-section, it is contemplated that the members can be, oval, triangular, square, rectangular, or other shape in cross-section.

The handle for the adjustable support of the present invention may be designed solely for use as a walking stick, solely for use as a crutch, for dual use as a walking stick and as a crutch. In order to be used as a crutch, the adjustable support will need to have a maximum extension long enough to fit under a user's armpit. In order to be used as a walking stick, the adjustable support need only be long enough to allow a user to grip and lean on the adjustable support.

The resilient base of the adjustable support of the present invention may be any conventional resilient base, such as the resilient bases used at the ends of canes, walking sticks, crutches, etc.

As shown in FIG. 14, three-member adjustable support 1400 includes a coarse adjustment device 1442. Coarse adjustment device 1442 is a conventional rotating locking mechanism that may be used to fix the position of middle member 1408 relative to outer member 1402, thereby providing coarse adjustment of adjustable support length $L_{14}$. Coarse adjustment device 1442 operates by rotating middle member 1408 relative to outer member 1402 until middle member 1408 is locked in place relative to outer member 1402.

Three-member adjustable support 1400 includes a fine adjustment device 1444. Fine adjustment device 1444 is comprised of a distal pulley post 1468, a proximal pulley post 1470, and a rope 1474 that extends through opening 1430 in handle 1428. Distal pulley post 1468 is mounted inside middle member 1408 and proximal pulley post 1470 is mounted to the inside of inner member 1414. Loops 1478 and 1480 of rope 1474 wrap around distal pulley post 1468 and proximal pulley post 1470, respectively. Rope 1474 is attached to inner member 1414 at attached end 1482 of rope 1474. Openings in inner member 1414 (not shown) allow for movement of inner member 1414 relative to middle member 1408 without inner member 1414 contacting distal pulley post 1468. A user of three-member adjustable support 1400 may pull on free end 1484 of rope 1474 to cause loops 1478 and 1480 of rope 1474 around distal pulley post 1468 and proximal pulley post 1470, respectively, to tighten and pull distal pulley post 1468 and proximal pulley post 1470 toward one another. Fine adjustment device 1444 allows for movement of inner member 1414 relative to middle member 1408 and provides fine adjustment of adjustable support length $L_{14}$.

Fine adjustment device 1444 also provides mechanical advantage that allows three-member adjustable support 1400 to be used to reduce fractures or dislocations in limbs secured to three-member adjustable support 1400 without requiring great strength or exertion by the user. Once a desired adjustable support length $L_{14}$ is achieved, free end 1484 may be secured at a cleat 1486 mounted on handle 1428. Fine adjustment device 1444 allows inner member 1414 to be moved relative to middle member 1408 and allows fine adjustment of adjustable support length $L_{14}$. Movement of inner member 1414 relative to middle member 1408 may be further restricted by using an external friction brake 1488 mounted on middle member 1408. External friction brake operates by compressing middle member 1408 against inner member 1414 until the friction between middle member 1408 and inner member 1414 is sufficient to prevent middle member 1408 and inner member 1414 from moving with respect to each other in a longitudinal direction. Preferably external friction brake compresses both middle member 1408 and inner member 1414. A similar external brake may be used instead of coarse adjustment device 1442 to fix position of middle member relative to outer member.

A preferred type of external friction brake for use in the present invention is described in U.S. Pat. No. 5,441,307 to Quintana et al., the entire contents and disclosure of which is hereby incorporated by reference. Although the Quintana et al friction brake operates by clamping the inner member within the middle, or by clamping the middle member within the outer, other types of friction brakes may be used, such as threaded friction brakes that compress middle member or inner member as the friction brake is rotated along a thread on the outer member or middle member, respectively.

The cleat of the adjustable support of FIG. 14 is shown at the outer member proximal end, but other locations on or in the splint may be utilized. The cleat may be a conventional cleat, a hook, or other suitable fastener for securing the rope. Other methods for locking the rope in position are tying a knot on the rope, or using a slidable device to engage the rope and restrict motion toward the splint, thereby maintaining traction.

Although the adjustable supports of FIGS. 12, 13 and 14 are three-member adjustable supports, the walking sticks or crutches of the present invention may be constructed as two-member adjustable supports similar to adjustable support shown in FIGS. 4A and 4B.

The adjustable supports shown in FIGS. 12, 13, and 14 may be strapped to an individual to provide traction to a user who has a broken limb. Alternatively, the adjustable supports may be simply be used as free supports, such as a conventional walking stick, cane or crutch.

Although the components in many of the embodiments of the adjustable support of the present invention shown above are shown in a semi- or completely transparent state for convenience of illustration, the actual materials used to construct the structures of the present invention may or may not be translucent or transparent. Materials appropriate for construction of the outer, middle, and inner members include: metal, preferably light yet strong metals such as aluminum or titanium, durable plastics, wood, etc. One of the benefits of the splint of the present invention is its ability to be readily transportable due to size and shape. Accordingly lighter materials are favored but the invention may still be practiced with heavier materials.

Although only a few types of adjustment devices are illustrated in the drawing figures and described above, the present invention encompasses various types of conventional adjustment devices that can be used to move two members relative to each other such as: hole-and-post-type devices, ratchet device, spring-loaded devices, pulley devices, screw-type devices, etc.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An adjustable support, comprising:
    an outer member having a distal end and a proximal end;
    a middle member slidable in a longitudinal direction within said outer member, said middle member having a distal end and a proximal end;
    an inner member slidable in a longitudinal direction within said middle member, said inner member having a distal end and a proximal end;
    a coarse adjustment means for adjusting a distance between said distal end of said middle member and a proximal end of said outer member by a plurality of course increments; and
    a fine adjustment means for adjusting a distance between said distal end of said inner member and a proximal end of said middle member by a plurality of fine increments.

2. The adjustable support of claim 1, wherein:
    said coarse adjustment means is comprised of a plurality of openings in said outer member and a spring loaded plunger mounted on said middle member for releasably and selectively engaging one of said openings in said outer member.

3. The adjustable support of claim 1, wherein said coarse adjustment means comprises:
    at least two paired opposed and aligned first openings in a first member selected from the group consisting of said outer member and said middle member;
    a plurality of paired opposed and aligned second openings in a second member from the group consisting of said outer member and said middle member, wherein said first member and said second member are not the same; and
    a post for engaging and extending through two of said paired first openings in said first member, and through two of said plurality of paired second openings in said second member for preventing longitudinal movement of said middle member relative to said outer member when said post extends through said paired first openings and said paired second openings.

4. The adjustable support of claim 1, wherein said fine adjustment means comprises:
    a plurality of ratchet slots on at least one side of said inner member;
    a ratchet for moving said inner member relative to said middle member by selectively engaging one of said ratchet slots on one side of said inner member through an opening in said middle member; and
    a brake for preventing motion of said distal end of said inner member toward said proximal end of said middle member when said ratchet is engaged with one of said ratchet slots on said inner member.

5. The adjustable support of claim 4, wherein said adjustable support further comprises a plurality of brake slots on at least one side of said inner member; and wherein said brake comprises:
    a lever pivotably attached to said middle member, said lever including:

an engaging end adapted for selectively engaging one of said plurality of brake slots;
a middle portion containing a pivotal attachment for pivotably securing said brake to said middle member; and
a resistance end attached to said middle member by a resistance means for providing resistance against compression of said lever towards said middle member.

6. The adjustable support of claim 1, wherein said fine adjustment means comprises a pulley system including:
a distal pulley post mounted inside said inner member;
a proximal pulley post mounted inside said middle member;
cord means, said cord means being looped at least once around said distal pulley post, being looped at least once around said proximal pulley post, having an attached end attached to said middle member and a free end extending from said adjustable support, so that when said free end is pulled, said distal pulley post and said proximal pulley post move towards each other and said distal end of said inner member and said proximal end of said middle member move away from each other.

7. The adjustable support of claim 6, wherein said free end of said cord means extends from said adjustable support through an opening in said inner member.

8. The adjustable support of claim 6, wherein said proximal pulley post and said distal pulley post are mounted at an offset angle with respect to each other.

9. The adjustable support of claim 6, wherein said proximal pulley post comprises a multi-prong pulley post.

10. The adjustable support of claim 6, wherein said distal pulley post comprises a multi-prong pulley post.

11. The adjustable support of claim 6, wherein both said proximal pulley post and said distal pulley post each comprise a multi-prong pulley post.

12. The adjustable support of claim 1, further comprising:
a distal securing means attached to said distal end of said inner member for securing said inner member to an individual's limb; and
a proximal securing means attached to said proximal end of said outer member for securing said outer member to an individual's limb.

13. The adjustable support of claim 12, wherein said distal securing means comprises a ring and said proximal securing means comprises a ring.

14. The adjustable support of claim 1, wherein said outer member, said middle member, and said inner member are each triangular in cross-section.

15. The adjustable support of claim 1, wherein said outer member, said middle member, and said inner member are each rectangular in cross-section.

16. The adjustable support of claim 1, wherein said outer member, said middle member, and said inner member are each circular in cross-section.

17. The adjustable support of claim 1, further comprising a handle mounted at a distal end or a proximal end of said adjustable support.

18. The adjustable support of claim 17, wherein said handle is mounted on said distal end of said inner member.

19. The adjustable support of claim 17, wherein said handle is mounted on said proximal end of said outer member.

20. The adjustable support of claim 17, wherein said handle comprises an armpit rest.

21. The adjustable support of claim 17, wherein said handle comprises a hand grip.

22. The adjustable support of claim 17, further comprising a resilient base mounted at said distal end or at said proximal end of said adjustable support.

23. The adjustable support of claim 22, wherein said resilient base is mounted on said proximal end of said outer member.

24. The adjustable support of claim 22, wherein said resilient base is mounted on said distal end of said inner member.

25. The adjustable support of claim 17, further comprising a foot rest mounted at said distal end or at said proximal end of said adjustable support.

26. The adjustable support of claim 25, wherein said foot rest is mounted on said proximal end of said outer member.

27. The adjustable support of claim 26, further comprising a stopper mounted on said proximal end of said outer member and mounted proximally of said footrest.

28. The adjustable support of claim 25, wherein said foot rest is mounted on said distal end of said inner member.

29. The adjustable support of claim 28, further comprising a stopper mounted on said distal end of said inner member and mounted distally of said footrest.

30. The adjustable support of claim 17, further comprising a hook mounted on said proximal or said distal end of said adjustable support for allowing a strap to be secured to said hook.

31. The adjustable support of claim 30, wherein said hook comprises a retractable hook.

32. The adjustable support of claim 17, further comprising a strap extending from said adjustable support for extending under the sole of a user's foot and for providing an even point of traction to a user's leg when a user s leg is secured to said adjustable support.

33. The adjustable support of claim 17, further comprising an external, friction brake mounted on said middle member for compressing said middle member against said inner member to prevent said inner member and said middle member from moving longitudinally with respect to each other.

34. An adjustable support, comprising:
an outer member having a distal end and a proximal end;
an inner member slidable in a longitudinal direction within said outer member, said inner member having a distal end and a proximal end; and
an adjustment means for adjusting a distance between said distal end of said inner member and a proximal end of said outer member by a plurality of fine increments, wherein said adjustment means comprises:
a plurality of ratchet slots on at least one side of said inner member;
a ratchet for moving said inner member relative to said outer member by selectively engaging one of said ratchet slots on one side of said inner member through an opening in said outer member; and
a brake for preventing motion of said distal end of said inner member toward said proximal end of said outer member when said ratchet is engaged with one of said ratchet slots on said inner member.

35. The adjustable support of claim 34, wherein said adjustable support further comprises a plurality of brake slots on at least one side of said inner member, and wherein said brake comprises:
a lever pivotably attached to said outer member, said lever including:
a engaging end adapted for selectively engaging one of said plurality of brake slots;

a middle portion containing a pivotal attachment for pivotably securing said brake to said outer member; and a resistance end attached to said outer member by a resistance means for providing resistance against compression of said lever towards said outer member.

36. An adjustable support, comprising:

an outer member having a distal end and a proximal end;

an inner member slidable in a longitudinal direction within said outer member, said inner member having a distal end and a proximal end; and an adjustment means for adjusting a distance between said distal end of said inner member and a proximal end of said outer member by a plurality of fine increments, wherein said adjustment means comprises a pulley system including:

a distal pulley post mounted inside said inner member;

a proximal pulley post mounted inside said outer member; and cord means, said cord means being looped at least once around said distal pulley post, being looped at least once around said proximal pulley post, having a attached end fixed to said inner member and a free end extending from said adjustable support, so that when said free end is pulled, said distal pulley post and said proximal pulley post move towards each other and said distal end of said inner member and said proximal end of said outer member move away from each other.

37. The adjustable support of claim 36, wherein said free end of said cord means extends from said adjustable support through an opening in said inner member.

38. The adjustable support of claim 36, wherein said proximal pulley post and said distal pulley post are mounted at an offset angle with respect to each other.

39. The adjustable support of claim 36, wherein said proximal pulley post comprises a multi-prong pulley post.

40. The adjustable support of claim 36, wherein said distal pulley post comprises a multi-prong pulley post.

41. The adjustable support of claim 36, wherein both said proximal pulley post and said distal pulley post each comprise a multi-prong pulley post.

42. An adjustable support, comprising:

an outer member having a distal end and a proximal end;

an inner member slidable in a longitudinal direction within said outer member, said inner member having a distal end and a proximal end;

an adjustment means for adjusting a distance between said distal end of said inner member and a proximal end of said outer member by a plurality of fine increments;

a distal securing means attached to said distal end of said inner member for securing said inner member to an individual's limb; and a proximal securing means attached to said proximal end of said outer member for securing said outer member to an individual's limb.

43. The adjustable support of claim 42, wherein said distal securing means comprises a ring and said proximal securing means comprises a ring.

44. An adjustable support, comprising:

an outer member having a distal end and a proximal end;

an inner member slidable in a longitudinal direction within said outer member, said inner member having a distal end and a proximal end; and an adjustment means for adjusting a distance between said distal end of said inner member and a proximal end of said outer member by a plurality of fine increments;

wherein said outer member and said inner member are each triangular in cross-section.

45. An adjustable support, comprising:

an outer member having a distal end and a proximal end;

an inner member slidable in a longitudinal direction within said outer member, said inner member having a distal end and a proximal end; and an adjustment means for adjusting a distance between said distal end of said inner member and a proximal end of said outer member by a plurality of fine increments;

wherein said outer member and said inner member are each rectangular in cross-section.

46. The adjustable support of claim 42, wherein said outer member and said inner member are each circular in cross-section.

47. The adjustable support of claim 42, further comprising a handle mounted at a distal end or a proximal end of said adjustable support.

48. The adjustable support of claim 47, wherein said handle is mounted on said distal end of said inner member.

49. An adjustable support, comprising:

an outer member having a distal end and a proximal end;

an inner member slidable in a longitudinal direction within said outer member, said inner member having a distal end and a proximal end;

an adjustment means for adjusting a distance between said distal end of said inner member and a proximal end of said outer member by a plurality of fine increments; and a handle mounted at a distal end or a proximal end of said adjustable support;

wherein said handle is mounted on said proximal end of said outer member.

50. The adjustable support of claim 47, wherein said handle comprises an armpit rest.

51. The adjustable support of claim 47, wherein said handle comprises a hand grip.

52. The adjustable support of claim 47, further comprising a resilient base mounted at said distal end or at said proximal end of said adjustable support.

53. The adjustable support of claim 52, wherein said resilient base is mounted on said proximal end of said outer member.

54. An adjustable support, comprising:

an outer member having a distal end and a proximal end;

an inner member slidable in a longitudinal direction within said outer member, said inner member having a distal end and a proximal end;

an adjustment means for adjusting a distance between said distal end of said inner member and a proximal end of said outer member by a plurality of fine increments;

a handle mounted at a distal end or a proximal end of said adjustable support; and a resilient base mounted on said proximal end of said outer member;

wherein said resilient base is mounted on said distal end of said inner member.

55. An adjustable support comprising:

an outer member having a distal end and a proximal end;

an inner member slidable in a longitudinal direction within said outer member, said inner member having a distal end and a proximal end;

an adjustment means for adjusting a distance between said distal end of said inner member and a proximal end of said outer member by a plurality of fine increments;

a handle-mounted at a distal end or a proximal end of said adjustable support; and a foot rest mounted at said distal end or at said proximal end of said adjustable support.

56. The adjustable support of claim 55, wherein said foot rest is mounted on said proximal end of said outer member.

57. The adjustable support of claim 56, further comprising a stopper mounted on said proximal end of said outer member and mounted proximally of said footrest.

58. The adjustable support of claim 55, wherein said foot rest is mounted on said distal end of said inner member.

59. The adjustable support of claim 58, further comprising a stopper mounted on said distal end of said inner member and mounted distally of said footrest.

60. An adjustable support comprising:

an outer member having a distal end and a proximal end;

an inner member slidable in a longitudinal direction within said outer member, said inner member having a distal end and a proximal end;

an adjustment means for adjusting a distance between said distal end of said inner member and a proximal end of said outer member by a plurality of fine increments;

a handle mounted at a distal end or a proximal end of said adjustable support; and a hook mounted on said proximal or said distal end of said adjustable support for allowing a strap to be secured to said hook.

61. The adjustable support of claim 60, wherein said hook comprises a retractable hook.

62. An adjustable support comprising:

an outer member having a distal end and a proximal end;

an inner member slidable in a longitudinal direction within said outer member, said inner member having a distal end and a proximal end;

an adjustment means for adjusting a distance between said distal end of said inner member and a proximal end of said outer member by a plurality of fine increments;

a handle mounted at a distal end or a proximal end of said adjustable support; and a strap extending from said adjustable support for extending under the sole of a user's foot and for providing an even point of traction to a user's leg when a user's leg is secured to said adjustable support.

63. An adjustable support comprising:

an outer member having a distal end and a proximal end;

a middle member slidable in a longitudinal direction within said outer member, said middle member having a distal end and a proximal end;

an inner member slidable in a longitudinal direction within said middle member, said inner member having a distal end and a proximal end;

an adjustment means for adjusting a distance between said distal end of said inner member and a proximal end of said outer member by a plurality of fine increments;

a handle mounted at a distal end or a proximal end of said adjustable support; and an external friction brake mounted on said middle member for compressing said middle member against said inner member to prevent said inner member and said middle member from moving longitudinally with respect to each other.

64. An adjustable support comprising:

an elongated member having a distal end and a proximal end;

a cord means extending through a hollow portion of said elongated member, said cord means including;

a distal securing means for securing said elongated member to a limb of an individual, said distal securing means being mounted at said distal end of said elongated member and including a loop portion extending form said distal end of said elongated member;

a free end for grasping by a user and for allowing a user to pull on said cord means to cause said loop portion of said distal securing means to pull the limb of the individual towards said elongated member;

a connecting portion connecting said loop portion of said distal securing means to said free end; and proximal securing means for securing said elongated member to the limb of the individual, said proximal securing means being mounted on said elongated member at a position proximal to said distal end of said elongated member.

65. The adjustable support of claim 64, wherein said elongated member comprises a hollow tube.

66. The adjustable support of claim 64, wherein said loop portion of said distal securing means includes a constriction loop for securing to the limb of the individual and a ring means for allowing sliding of said cord means for connecting said cord and said constriction loop.

* * * * *